US007662770B2

(12) United States Patent
Kinch

(10) Patent No.: US 7,662,770 B2
(45) Date of Patent: Feb. 16, 2010

(54) LOW MOLECULAR WEIGHT PROTEIN TYROSINE PHOSPHATASE (LMW-PTP) AS A DIAGNOSTIC AND THERAPEUTIC TARGET

(75) Inventor: Michael S. Kinch, Laytonville, MD (US)

(73) Assignee: Purdue Research Foundation, West LaFayette, IN (US)

( * ) Notice: Subject to any disclaimer, the term of this patent is extended or adjusted under 35 U.S.C. 154(b) by 350 days.

(21) Appl. No.: 10/515,358

(22) PCT Filed: May 22, 2003

(86) PCT No.: PCT/US03/16269

§ 371 (c)(1),
(2), (4) Date: Aug. 11, 2005

(87) PCT Pub. No.: WO03/099313

PCT Pub. Date: Dec. 4, 2003

(65) Prior Publication Data

US 2006/0093608 A1 May 4, 2006

Related U.S. Application Data

(60) Provisional application No. 60/382,988, filed on May 23, 2002.

(51) Int. Cl.
*A61K 38/00* (2006.01)
(52) U.S. Cl. ........................................................ 514/2
(58) Field of Classification Search ...................... 514/2
See application file for complete search history.

(56) References Cited

U.S. PATENT DOCUMENTS

| | | | |
|---|---|---|---|
| 5,876,949 | A | 3/1999 | Dreyfuss et al. |
| 5,958,957 | A | 9/1999 | Andersen et al. |
| 6,927,203 | B1 | 8/2005 | Kinch et al. |
| 7,101,976 | B1 | 9/2006 | Kilpatrick et al. |
| 7,192,698 | B1 | 3/2007 | Kinch et al. |
| 7,479,368 | B2 | 1/2009 | Brown et al. |
| 7,485,420 | B2 | 2/2009 | Markowitz |
| 7,507,418 | B2 | 3/2009 | Atkinson et al. |
| 2004/0028685 | A1 | 2/2004 | Kinch et al. |
| 2004/0091486 | A1 | 5/2004 | Kinch et al. |
| 2005/0147593 | A1 | 7/2005 | Kinch |
| 2005/0152899 | A1 | 7/2005 | Kinch et al. |
| 2005/0153923 | A1 | 7/2005 | Kinch |
| 2005/0169931 | A1 | 8/2005 | Kinch et al. |
| 2006/0088541 | A1 | 4/2006 | Kinch et al. |
| 2006/0093608 | A1 | 5/2006 | Kinch |
| 2007/0086943 | A1 | 4/2007 | Kinch et al. |
| 2008/0089931 | A1 | 4/2008 | Kinch |

FOREIGN PATENT DOCUMENTS

| EP | 1242060 B1 | 5/2006 |
|---|---|---|
| EP | 1695702 A2 | 8/2006 |
| WO | WO 01/12172 A1 | 2/2001 |
| WO | WO 01/12840 A2 | 2/2001 |
| WO | WO 03/094859 A2 | 11/2003 |
| WO | WO 03/099313 A1 | 12/2003 |
| WO | WO 2004/014292 A2 | 2/2004 |
| WO | WO 2004/014292 A3 | 2/2004 |
| WO | WO 2005/051307 A2 | 6/2005 |
| WO | WO 2005/051307 A3 | 6/2005 |
| WO | WO 2005/055948 A2 | 6/2005 |
| WO | WO 2005/055948 A3 | 6/2005 |
| WO | WO 2005/056766 A2 | 6/2005 |

OTHER PUBLICATIONS

Carles-Kinch et al., "Antibody targeting of the EphA2 tyrosine kinase inhibits malignant cell behavior," May 15, 2002 *Cancer Research* 62(10):2840-2847.
Park et al., "Low-molecular-weight protein tyrosine phosphatase is a positive component of the fibroblast growth factor receptor signaling pathway," May 15, 2002 *Molecular and Cellular Biology* 22(10):3404-3414.
Souza et al., "From immune response to cancer: a spot on the low molecular weight protein tyrosine phosphatase," Apr. 2009 *Cellular and Molecular Life Sciences* 66(6):1140-1153. Available online on Nov. 11, 2008.
Supplementary European Search Report mailed Jun. 8, 2009, for EP Application No. 03734142.7 (3 pgs).
Cann, "Genetic clues to dispersal in human populations: retracting the past from the present," Mar. 2, 2001 *Science* 291:1742-1748.
Garcia-Closas et al., "Collection of genomic DNA from adults in epidemiological studies by buccal cytobrush and mouthwash," Jun. 2001 *Cancer Epidemiology, Biomarkers & Prevention* 10:687-696.
National Center for Biotechnology Information, National Library of Medicine, National Institutes of Health. GenBank Locus NM_007099, Accession No. NM_007099, Version NM_007099.1 GI:6005987, "*Homo sapiens* acid phophatase 1, soluble (ACP1), transport variant b, mRNA," [online]. Bethesda, MD [retrieved on Mar. 26, 2008]. Retrieved from the Internet: <http://www.ncbi.nlm.nih.gov/entrez/viewer.fcgi?6005987:OLD12:570167>; 3 pgs.
National Center for Biotechnology Information, National Library of Medicine, National Institutes of Health, GenPept Locus P24666, Accession No. P24666, Version P24666 GI:1709543, "Red cell acid phosphatase 1, isoenzyme F (ACP1) (Low molecular weight phosphotyrosine phosphatase) (Adipocyte acid phosphatase, isoenzyme alpha)," [online]. Bethesda. MD [retrieved on Mar. 25, 2008]. Retrieved from the Internet: <http://www.ncbi.nlm.nih.gov/entrez/viewer.fcgi?1709543:OLD11:669086>; 4 pgs.
Åkerud et al., "Intramolecular Dynamics of Low Molecular Weight Protein Tyrosine Phosphatase in Monomer-Dimer Equilibrium Studied by NMR: A Model for Changes in Dynamics Upon Target Binding," *J. Mol. Biol.*, Sep. 6, 2002; 322(1):137-152.

(Continued)

*Primary Examiner*—Christopher H Yaen
(74) *Attorney, Agent, or Firm*—Mueting Raasch & Gebhardt, P.A.

(57) ABSTRACT

Low molecular weight protein tyrosine phosphatase (LMW-PTP) is identified as a novel diagnostic and therapeutic target in cancer diagnosis, prognosis and treatment. The invention provides diagnostic and treatment methods useful in connection with cancers expressing LMW-PTP and, optionally, EphA2 receptor. Also provided is a screening method that utilizes changes in the amount and/or activity of LMW-PTP to identify candidate cancer therapeutic agents that effectively target the oncoprotein EphA2.

15 Claims, 22 Drawing Sheets

OTHER PUBLICATIONS

Andres et al., "Expression of Two Novel *eph*-related Receptor Protein Tyrosine Kinases in Mammary Gland Development and Carcinogenesis," *Oncogene*, May 1994;9:1461-1467.

Arakawa et al., "Genomic Organization of the *Klebsiella pneumoniae cps* Region Responsible for Serotype K2 Capsular Polysaccharide Synthesis in the Virulent Strain Chedid," *J. Bacteriol.*, Apr. 1995;177(7):1788-1796. Available online at Journal of Bacteriology [retrieved Oct. 25, 2006]. Retrieved from the Internet:<URL:http://jb.asm.org/cgi/reprint/177/7/1788>; 9 pgs.

Boivin et al., "The Human Red Cell Acid Phosphatase Is a Phosphotyrosine Protein Phosphatase Which Dephosphorylates the Membrane Protein Band 3," *Biochem. Biophys. Res. Commmun.*, Jan. 29, 1986;134(2):557-564.

Bugert et al., "Characterization of the *ams*1 Gene Product as a Low Molecular Weight Acid Phosphatase Controlling Exopolysaccharide Synthesis of *Erwinia amylovora*," *FEBS Lett.*, Jan. 1997;400(2):252-256.

Brackenbury, "Control of Carcinoma Cell Motility by E-Cadherin," Abstract and Final Report, Grant No. DAMD 17-98-1-8292; United States Army Medical Research and Material Command Grant, project dates Aug. 1, 1998 to Jul. 31, 2002 [retrieved on Jun. 7, 2007]. Retrieved from the Internet:<URL:http://stinet.dtic.mil/oai/oai?&verb=getRecord&metadataPrefix=html&identifier=ADA409404>; 31 pgs.

Caselli et al., "The Inactivation Mechanism of Low Molecular Weight Phosphotyrosine-protein Phosphatase by $H_2O_2$," *J. Biol. Chem.*, Dec. 4, 1998; 273(49): 32554-32560. Available online at JBC Online [retrieved Oct. 25, 2006]. Retrieved from the Internet:<URL:http://www.jbc.org/cgi/reprint/273/49/32554>; 7 pgs.

Chernoff et al., "A Major Phosphotyrosyl-Protein Phosphatase from Bovine Heart is Associated with a Low-Molecular-Weight Acid Phosphatase," *Arch. Biochem. Biophys.*, Jul. 1985;240(1):135-145.

Chiaraugi et al., "The Src and Signal Transducers and Activators of Transcription Pathways As Specific Targets for Low Molecular Weight Phosphotyrosine-protein Phosphatase in Platelet-derived Growth Factor Signaling," *J. Biol. Chem.*, Mar. 20, 1998;273(12):6776-6785.

Clark et al., "Overexpression of the Ras-related TC21/R-Ras2 Protein May Contribute to the Development of Human Breast Cancers," *Oncogene*, 1996 12(1):169-176.

Corden et al. "Low Molecular Weight Phosphatase," Abstract, p. 20 of Project Detail, General Basic Research in the Walther Cancer Center of Excellence [online]. Walther Cancer Institute, Indianapolis, IN, project dates Jul. 1, 2004 to Jun. 30, 2005 [retrieved on Jun. 5, 2007]. Retrieved from the Internet:<URL:www.walther.org/wcf_scipro/wcf_projects/15.html>; 44 pgs.

Davis et al., "Kinetic and Site-directed Mutagenesis Studies of the Cysteine Residues of Bovine Low Molecular Weight Phosphotyrosyl Protein Phosphatase," *J. Biol. Chem.*, Mar. 25, 1994;269(12):8734-8740. Available online at JBC Online [retrieved Oct. 25, 2006]. Retrieved from the Internet:<URL:http://www.jbc.org/cgi/reprint/269/12/8734>; 7 pgs.

Dissing et al., "Human Red Cell Acid Phosphatase: Purification and Properties of the A, B, and C Isozymes," *Biochem. Biophys. Acta.*, Dec. 5, 1990;1041(3):232-242.

Easty et al., "Protein Tyrosine Kinases in Malignant Melanoma," *Melanoma Res.*, Oct. 2000;10(5):401-411.

Eph Nomenclature Committee, 1997, "Unified Nomenclature for Eph Family Receptors and Their Ligands, the Ephrins," *Cell*, Aug. 8, 1997;90(3):403-404.

Fiaschi et al., "Low Molecular Weight Protein-tyrosine Phosphatase Is Involved in Growth Inhibition during Cell Differentiation," *J. Biol. Chem.*, Dec. 28, 2001;276(52):49156-49163; electronically published Oct. 10, 2001. Available online at JBC Online [retrieved Oct. 25, 2006]. Retrieved from the Internet:<URL:http://www.jbc.org/cgi/reprint/276/52/49156>; 8 pgs.

Gaits et al., "Implication of a Protein-Tyrosine-Phosphatase in Human Lung Cancer," *Cell. Mol. Biol.*, Jul. 1994;40(5):677-685.

Gilardi-Hebenstreit et al., "An Eph-related Receptor Protein Tyrosine Kinase Gene Segmentally Expressed in the Developing Mouse Hindbrain," *Oncogene*, Dec. 1992;7(12):2499-2506.

Gustafson et al., "Solution Structure of the Low Molecular Weight Protein Tyrosine Phosphatase From *Tritrichomonas foetus* Reveals a Flexible Phosphate Binding Loop," *Protein Sci.*, Oct. 2005; 14(10):2515-2525.

Heinrikson, "Purification and Characterization of a Low Molecular Weight Acid Phosphatase from Bovine Liver," *J. Biol. Chem.*, 1969;244(2):299-307. Available online at JBC Online [retrieved Oct. 25, 2006]. Retrieved from the Internet:<URL:http://www.jbc.org/cgi/reprint/244/2/299>; 9 pgs.

Hess et al., "Molecular Regulation of Tumor Cell Vasculogenic Mimicry by Tyrosine Phosphorylation: Role of Epithelial Cell Kinase (Eck/EphA2)," *Cancer Res*, Apr. 15, 2001;61(8):3250-3255.

Hirai et al., "A Novel Putative Tyrosine Kinase Receptor Encoded by the *eph* Gene," *Science*, Dec. 18, 1987;238(4834):1717-1720.

Huang et al., "HCPTPA, a Protein Tyrosine Phosphatase That Regulates Vascular Endothelial Growth Factor Receptor-Mediated Signal Transduction and Biological Activity," *J. Biol. Chem.*, Dec. 31, 1999;274(53):38183-38188.

Jacob et al., "A Receptor Tyrosine Kinase, UFO/Axl, and Other Genes Isolated by a Modified Differential Display PCR Are Overexpressed in Metastatic Prostatic Carcinoma Cell Line DU145," *Cancer Detect Prev.*, 1999;23(4):325-332.

Kikawa et al., "Regulation of the EphA2 Kinase by the Low Molecular Weight Tyrosine Phosphatase Induces Transformation," *J. Biol. Chem.*, Oct. 18, 2002;277(42):39274-39279; electronically published Aug. 6, 2002.

Kinch et al., "Tyrosine Phosphorylation Regulates the Adhesions of Ras-Transformed Breast Epithelia," *J. Cell Biol.*, Jul. 1995;130(2):461-471.

Kinch, Michael, "EphA2—A Marker of Breast Cancer Progression," Grant Abstract, Grant No. 5R21CA85615-02 [online]. National Cancer Institute, project dates Apr. 1, 2000 to Mar. 31, 2002 [retrieved Sep. 22, 2006]. Retrieved from the Internet:<URL:http://crisp.cit.nih.gov/>; 2 pgs.

Kinch et al., "Overexpression and Functional Alterations of the EphA2 Tyrosine Kinase in Cancer," *Clin. Exp. Metastasis*, 2003;20(1):59-68.

Kinch et al., "Predictive Value of the EphA2 Receptor Tyrosine Kinase in Lung Cancer Recurrence and Survival," *Clin. Cancer Res.*, Feb. 2003;9(2):613-618.

Lindberg et al., "cDNA Cloning and Characterization of *eck*, an Epithelial Cell Receptor Protein-Tyrosine Kinase in the *eph/elk* Family of Protein Kinases," *Mol. Cell. Biol.* Dec. 1990;10(12):6316-6324.

Manao et al., "Rat Liver Low $M_r$ Phosphotyrosine Protein Phosphatase Isoenzymes: Purification and Amino Acid Sequences," *J. Protein Chem.*, Jun. 1992;11(3):333-345.

Mondesert et al., "Low Molecular Weight Protein-tyrosine Phosphatases Are Highly Conserved between Fission Yeast and Man," *J. Biol. Chem.*, Nov. 11, 1994;269(45):27996-27999. Available online at JBC Online [retrieved on Oct. 25, 2006]. Retrieved from the Internet:<URL:http://www.jbc.org/cgi/reprint/269/45/27996>; 4 pgs.

Ogawa et al., "The Ephrin-A1 Ligand and Its Receptor, EphA2, Are Expressed During Tumor Neovascularization," *Oncogene*, 2000; 19:6043-6052.

Ostanin et al., "Cloning and Characterization of a *Saccharomyces cerevisiae* Gene Encoding the Low Molecular Weight Protein-tyrosine Phosphatase," *J. Biol. Chem.*, Aug. 4, 1995;270(31):18491-18499. Available online at JBC Online [retrieved on Oct. 25, 2006]. Retrieved from the Internet:<URL:http://www.jbc.org/cgi/reprint/270/31/18491>; 9 pgs.

Paine et al., "Characterization of Epithelial Phenotypes in Mortal and Immortal Human Breast Cells," *Int. J. Cancer*, 1992; 50:463-473.

Ruggiero et al., "Negative Growth Control by a Novel Low $M_r$ Phosphotyrosine Protein Phosphatase in Normal and Transformed Cells," *FEBS Lett.*, Jul. 12, 1993;326(1-3):294-298. Available online at Science Direct [retrieved Oct. 25, 2006]. Retrieved from the Internet: <URL:http://www.sciencedirect.com>; 5 pgs.

Sajjadi et al., "Identification of a New *eph*-Related Receptor Tyrosine Kinase Gene From Mouse and Chicken That Is Developmentally Regulated and Encodes At Least Two Forms of the Receptor," The New Biologist, Aug. 1991, 3(8):769-778.

Schroff, "Investigations into the Physiological Role of the Human Low Molecular Weight Phosphotyrosyl Protein Phosphatase," Ph.D. Thesis, Purdue University, West Lafayette, Indiana; 294 pgs., Dec. 1997.

Shevrin et al., "Patterns of Metastasis by the Human Prostate Cancer Cell Line PC-3 in Athymic Nude Mice," *The Prostate*, 1989;15(2):187-194.

Shimizu et al., "Low $M$ Protein Tyrosine Phosphatase Inhibits Growth and Migration of Vascular Smooth Muscle Cells Induced by Platelet-Derived Growth Factor," *Biochem. Biophy. Res. Commun.*, Nov. 30, 2001;289(2):602-607.

Stauffacher et al., "Computationally Designed Inhibitors of the Low Molecular Weight Phosphatase HCPTP," XIX Congress and General Assembly of the International Union of Crystallography, Geneva, Switzerland Aug. 6-15, 2002; *Acta Cryst.* Aug. 2002; 58 (Supplement): C62. Available at Crystallography Journals Online [retrieved on Sep. 21, 2006]. Retrieved from the Internet:<URL:http://www.fr.iucr.org/a/issues/2002/s1/00/a29928/a29928.pdf>; 3 pgs.

Stein et al., "Eph Family Receptors and Ligands in Vascular Cell Targeting and Assembly," *Trends Cardiovasc. Med.*, Nov. 1997;7(8):329-334.

Stein et al., "Eph Receptors Discriminate Specific Ligand Oligomers to Determine Alternative Signaling Complexes, Attachment, and Assembly Responses," *Genes Dev.*, Mar. 1, 1998;12(5):667-678.

Stevenson et al., "Organization of the *Escherichia coli* K-12 Gene Cluster Responsible for Production of the Extracellular Polysaccharide Colanic Acid," *J. Bacteriol.*, Aug. 1996;178(16):4885-4893. Available online at Journal of Bacteriology [retrieved Oct. 25, 2006]. Retrieved from the Internet:<URL:http://jb.asm.org/cgi/reprint/178/16/4885>; 9 pgs.

Tabernero et al., "The Structure of the Bovine Protein Tyrosine Phosphatase Dimer Reveals a Potential Self-Regulation Mechanism," *Biochemistry*, Sep. 7, 1999; 38(36):11651-11658.

U66070: National Center for Biotechnology Information, National Library of Medicine, National Institutes of Health, GenBank Locus TFU66070, Accession No. U66070, "Tritrichomonas foetus putative protein tyrosine phosphatase, complete cds, and putative serine/threonine protein kinase genes, partial cds.," [online]. Bethesda, MD [retrieved on Aug. 28, 2006]. Retrieved from the Internet:<URL:http://www.ncbi.nlm.nih.gov/entrez/viewer.fcgi?db= nucleotide&val=1915988>; 2 pgs.

Vidale, "Protein-Protein Interactions Involving Human Low Molecular Weight Protein Tyrosine Phosphatase and EphA2," M.S. Thesis, Purdue University, West Lafayette, Indiana; 81 pgs., Cover date: Dec. 2000. Confidential hold released on Jun. 30, 2002.

Waheed et al., "Purification and Physicochemical Characterization of a Human Placental Acid Phosphatase Possessing Phosphotyrosyl Protein Phosphatase Activity," *Biochemistry*, Jun. 14, 1988;27(12):4265-4273.

Walker-Daniels et al., "Overexpression of the EphA2 Tyrosine Kinase in Prostate Cancer," *The Prostate.*, Dec. 1, 1999;41(4):275-280.

Walker-Daniels et al., "c-Cbl-Dependent EphA2 Protein Degradation Is Induced by Ligand Binding," *Mol. Cancer Res.*, Nov. 2002;1(1):79-87.

Walker-Daniels et al., "Differential Regulation of EphA2 in Normal and Malignant Cells," *Am. J. Pathol.*, Apr. 2003;162(4):1037-1042.

Wang et al., "Structural and Mechanistic Basis for the Activation of a Low-Molecular Weight Protein Tyrosine Phosphatase by Adenine," *Biochemistry*, Feb. 15, 2000;39(6):1234-1242.

Wang et al., "Crystal Structures of a Low-Molecular Weight Protein Tyrosine Phosphatase From *Saccharomyces cerevisiae* and Its Complex With the Substrate P-nitrophenyl Phosphate," *Biochemistry*, Feb. 29, 2000;39(8):1903-1914.

Wilbanks et al., "Rod Structure of a Phycoerythrin II-containing Phycobilisome. 1. Organization and Sequence of the Gene Cluster Encoding the Major Phycobiliprotein Rod Components in the Genome of Marine *Synechococcus* SP. WH8020," *J. Biol. Chem.*, Jan. 15, 1993;268(2):1226-1235. Available online at JBC Online [retrieved on Oct. 25, 2006]. Retrieved from the Internet:<URL:http://www.jbc.org/cgi/reprint/268/2/1226>; 10 pgs.

Wo et al., "Cloning, Expression and Catalytic Mechanism of the Low Molecular Weight Phosphotyrosyl Protein Phosphatase from Bovine Heart," *Biochemistry*, Feb. 18, 1992;31(6):1712-1721.

Wo, "Cloning, Expression, and Characterization of Low-Molecular-Weight Acid Phosphatases from Bovine Heart and Human Placenta," Ph.D Thesis, Purdue University, 1992.

Zabell et al., "Design and Synthesis of Tyrosine Phosphatase Inhibitor Directed Toward New Cancer Treatments," Abstract 130, 224th American Chemical Society National Meeting, Boston, MA, Aug. 18-22, 2002, Abstracts of Papers of the American Chemical Society, Part 2, 2002; 3 pages.

Zabell et al., "Computationally Designed Inhibitors of the Interaction Between EphA2 and HCPTP," Poster, 47th Annual Meeting of the Biophysical Society, San Antonio, TX (Mar. 1-5, 2003), 2 pgs.

Zabell et al., "Crystal Structure of the B Isoform of the Human Low Molecular Weight Protein Tyrosine Phosphatase," Poster P008, Poster Session II, Jul. 27-30, Annual Meeting of the American Crystallographic Association, Cincinnati, OH (Jul. 26-31, 2003), 4 pgs.

Zabell et al., "Inhibition Studies with Rationally Designed Inhibitors of the Human Low Molecular Weight Protein Tyrosine Phosphatase," *Bioorganic & Medicinal Chemistry*, Apr. 15, 2004;12(8):1867-1880.

Zabell et al., "Structural and Kinetic Analysis of Human Low Molecular Weight Protein Tyrosine Phosphatase Inhibitors," Presentation No. 1599-Pos; Poster Board No. B584, Biophysical Society 48th Annual Meeting, Baltimore, MD, Feb. 14-18, 2004, Biophysical Journal, 2004;86:309. Abstract available on the Internet:<URL:http://www.abstractsonline.com> [retrieved on Sep. 20, 2006] 3 pages.

Zabell et al., "Structural and Kinetic Analysis of Human Low Molecular Weight Protein Tyrosine Phosphatase Inhibitors," Walther Cancer Institute Annual Scientific Retreat, Notre Dame, South Bend, IN (Aug. 5-7, 2004), 2 pgs.

Zabell et al., "Crystal Structure of the Human B-form Low Molecular Weight Phosphotyrosyl Phosphatase at 1.6-Å Resolution," *J. Biol. Chem.*, Mar. 10, 2006;281(10):6520-6527; electronically published Oct. 27, 2005.

Zabell et al., "Expression and Purification of the Intact Cytoplasmic Domain of the Human Ephrin Receptor A2 Tyrosine Kinase in *Escherichia coli*," *Protein Expr. Purif.*, May 2006; 47(1):210-216; electronically published Oct. 20, 2005.

Zantek et al., "Epithelial Cell Kinase (ECK / EphA2) Regulation in Breast Cancer," 38th Annual Meeting of the American Society for Cell Biology: Dec. 12-16, 1998. Abstrct 773. Published in 134a—Cell Adhesion and Signaling, *Molecular Biology of the Cell*, Nov. 1998; 9 (1 pg).

Zantek, "Regulation of the EphA 2 Receptor Tyrosine Kinase by Estrogen and Myc," Abstract #4537, 90th *Annual Meeting of the American Association for Cancer Research*, Philadelphia, PA, Apr. 10-14, 1999, published in Proceedings of the American Association for Cancer Research, Mar. 1999;40:687 (1 pg).

Zantek, "*Regulation of EphA2 and Focal Adhesion Kinase in Breast Cancer,*" Ph.D. Thesis, Purdue University, West Lafayette, Indiana; 136 pgs., Cover date: May 1999. Confidential hold released on Nov. 8, 2000.

Zantek et al., "E-Cadherin Regulates the Function of the EphA2 Receptor Tyrosine Kinase," *Cell Growth & Differentiation*, Sep. 1999;10:629-638.

Zantek et al., "MCF-10A-NeoST: A New Cell System for Studying Cell-ECM and Cell-Cell Interactions in Breast Cancer," *Clin. Cancer Res.*, Nov. 2001;7(11):3640-3648.

Zelinski et al., "EphA2 Overexpression in Breast Cancer: Regulation by Estrogen and c-Myc," Abstract #2275; 91st Annual Meeting of the American Association for Cancer Research, San Francisco, CA, Apr. 1-5, 2000, published in *Proceedings of the American Association for Cancer Research Annual Meeting*, Mar. 2000;41:358; 3 pages.

Zelinski et al., "EphA2 Overexpression Causes Tumorigenesis of Mammary Epithelial Cells," *Cancer Res.*, Mar. 1, 2001;61(5):2301-2306. Available online at Cancer Research [retrieved on Oct. 25, 2006]. Retrieved from the Internet:<URL:http://cancerres.aacrjournals.org/cgi/reprint/61/5/2301>; 6 pgs.

Zelinski et al., "EphA2 Overexpression Alters Cellular Adhesions: Implications for Metastasis," Abstract, FASEB Experimental Biology Conference, Orlando, FL, Mar. 31-Apr. 4, 2001; *FASEB J.* Mar. 7, 2001;15(4):A234, Abstract No. 211.4; 4 pages.

Zelinksi et al., "Estrogen and Myc Negatively Regulate Expression of the EphA2 Tyrosine Kinase," *J. Cell. Biochem.*, 2002;85(4):714-720.

Zhang et al., "Purification and Characterization of a Low-Molecular-Weight Acid Phosphatase—A Phosphotyrosyl-Protein Phosphatase from Bovine Heart," *Arch. Biochem. Biophys.*, Oct. 1990;282(1):39-49.

Zhang et al., "Crystallization and Preliminary X-ray Analysis of the Low Molecular Weight Phosphotyrosyl Protein Phosphatase From Bovine Heart," *J. Mol. Biol.*, Apr. 29, 1994:238(2):281-283.

Zhang et al., "Crystal Structure of Bovine Heart Phosphotyrosyl Phosphatase at 2.2-Å Resolution," *Biochemistry*, Sep. 20, 1994;33(37):11097-11105.

Zhang et al., "Asp$^{129}$ of Low Molecular Weight Protein Tyrosine Phosphatase Is Involved in Leaving Group Protonation," *J. Biol. Chem.* Oct. 21, 1994;269(42):25947-25950. Available online at JBC Online [retrieved on Oct. 25, 2006]. Retrieved from the Internet: <URL:http://www.jbc.org/cgi/reprint/269/42/25947>; 4 pgs.

Zhang et al., "The Three Dimensional Structure, Chemical Mechanism and Function of the Low Molecular Weight Protein Tyrosine Phosphatases," *Adv. Prot. Phosphatases*, 1995;9:1-23.

Zhang, "Crystallographic Structure Determination of Bovine Heart and Human Cytosolic Phosphotyrosyl Phosphatase," Ph.D. Thesis Purdue University, West Lafayette, Indiana, 1995; 173 pgs.

Zhang et al., "Crystal Structure of Bovine Low Molecular Weight Phosphotyrosyl Phosphatase Complexed with the Transition State Analog Vanadate," *Biochemistry*; Jan. 7, 1997;36(1):15-23.

Zhang et al., "Crystal Structure of Human Low Molecular Weight Phosphotyrosyl Phosphatase. Implications for Substrate Specificity," *J. Biol. Chem.*, Aug. 21, 1998;273(34):21714-21720. Available online at JBC Online [retrieved on Sep. 22, 2006]. Retrieved from the Internet:<URL:http://www.jbc.org/cgi/reprint/273/34/21714.pdf>; 7 pgs.

Zhang et al., "Characterization of a Prostate-specific Tyrosine Phosphatase by Mutageneis and Expression in Human Prostate Cancer Cells," *J. Biol. Chem.* Jan. 20, 2001;276(4):2544-2550; electronically published Nov. 6, 2000. Available online at JBC Online [retrieved on Oct. 25, 2006]. Retrieved from the Internet:<URL:http://www.jbc.org/cgi/content/full/276/54/2544>; 7 pgs.

Zhou et al., "Isolation and Characterization of *Bsk*, a Growth Factor Receptor-Like Tyrosine Kinase Associated with the Limbic System," *J. Neurosci. Res.*, Jan. 1994;37(1):129-143.

Zhou et al., "Structural Basis of the Tight Binding of Pyridoxal 5'—Phosphate to a Low Molecular Weight Protein Tyrosine Phosphatase," *Biochemistry*, Mar. 2, 1999;38(9):2636-2646.

Fig. 10
LMW-PTP overexpression alters two-dimensional morphology
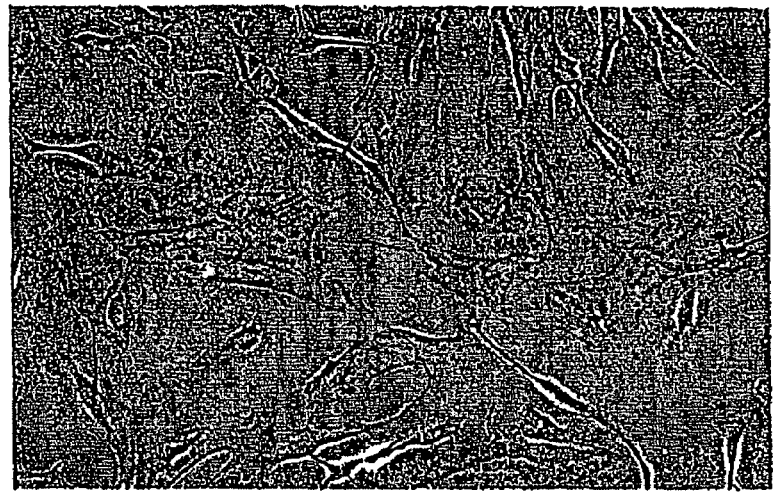
LMW-PTP
Vector Fig. 11 — LMW-PTP overexpressing cells form foci at high cell density Fig. 13 Inactivation of LMW-PTP alters two-dimensional morphology and EphA2 distribution in transformed cells

Fig. 15

Summary of Findings

| Cell | Soft Agar | EphA2 Expression | EphA2 Distribution | Actin | Paxillin | Cytokeratin | Vimentin |
|---|---|---|---|---|---|---|---|
| MCF-10 | No | Low | Cell-Cell | Belts | Periph FA | Yes | No |
| MCF-10A -LMW-PTP | Yes | High | Diffuse | Stress Fiber (SF) | Polar FA | No | Yes |
| MDA-MB-231 | Yes | High | Diffuse | Scattered SF | Polar FA | No | Yes |
| MDA-MB-231 – LMW-PTP$^{D129A}$ | No | Low | Cell-Cell | Belts | Periph FA | No | Yes |

```
                        SEQUENCE LISTING

<160> NUMBER OF SEQ ID NOS: 3

<210> SEQ ID NO 1
<211> LENGTH: 35
<212> TYPE: DNA
<213> ORGANISM: artificial
<220> FEATURE:
<223> OTHER INFORMATION: primer

<400> SEQUENCE: 1
aatttaaagc ttccatggcg gaacaggcta ccaag                              35

<210> SEQ ID NO 2
<211> LENGTH: 34
<212> TYPE: DNA
<213> ORGANISM: artificial
<220> FEATURE:
<223> OTHER INFORMATION: primer

<400> SEQUENCE: 2
cgttcttgga gaaggcccac tgagaattct tcgt                               34

<210> SEQ ID NO 3
<211> LENGTH: 28
<212> TYPE: DNA
<213> ORGANISM: artificial
<220> FEATURE:
<223> OTHER INFORMATION: primer

<400> SEQUENCE: 3
gcgcgcggat cctcagtggg ccttctcc                                      28
```

LOW MOLECULAR WEIGHT PROTEIN TYROSINE PHOSPHATASE (LMW-PTP) AS A DIAGNOSTIC AND THERAPEUTIC TARGET

This application claims the benefit of U.S. Provisional Application Ser. No. 60/382,988; filed May 23, 2002, which is incorporated herein by reference in its entirety.

This application also incorporates by reference the following U.S. patent applications in their entirety: Ser. No. 09/640,952, filed Aug. 17, 2000; Ser. No. 09/640,935, filed Aug. 17, 2000; and Ser. No. 09/952,560, filed Sep. 12, 2001.

BACKGROUND OF THE INVENTION

Cancer arises when a population of cells gains the ability to inappropriately grow and survive. These biological behaviors often result from genetic and environmental abnormalities that work together to trigger specific signaling pathways that promote the inappropriate growth and survival of malignant cells. In particular, protein tyrosine phosphorylation is understood to initiate powerful signals that govern many different aspects of cell behavior. A popular paradigm suggests that a balance between tyrosine kinase and phosphatase activities serves to dictate the cellular levels of protein tyrosine phosphorylation and thereby governs cellular decisions regarding growth, survival and invasiveness. This paradigm generally predicts that tyrosine kinases would be oncogenic whereas tyrosine phosphatases negatively regulate malignant transformation. Although this portioning is generally correct, emerging evidence reveals a more complex interplay between tyrosine kinases and phosphatases. For example, the PTP-CAAX tyrosine phosphatase has been recently shown to function as a powerful oncogene. Moreover, the enzymatic activity of Src family kinases is liberated by phosphatase-mediated dephosphorylation of important tyrosine residues. In the latter situation, phosphatases can actually up-regulate protein tyrosine phosphorylation by increasing the enzymatic activity of kinases:

The EphA2 receptor tyrosine kinase is overexpressed in a large number of human cancers. High levels of EphA2 apply to a large number of different cancers, including breast, prostate, colon and lung carcinomas as well as metastatic melanomas. Moreover, the highest levels of EphA2 are consistently found on the most aggressive cell models of human cancer. EphA2 is not simply a marker of malignant disease as ectopic overexpression of EphA2 is sufficient to confer tumorigenic and metastatic upon non-transformed epithelial cells.

Cancer cells also display differences in EphA2 function as compared with non-transformed epithelia. Despite being present at relatively low levels in non-transformed epithelial cells, EphA2 in these cells is prominently tyrosine phosphorylated. In contrast, the EphA2 in malignant cells is not tyrosine phosphorylated even though it is grossly overexpressed in these cells. These differences in EphA2 phosphotyrosine content are important because tyrosine phosphorylated EphA2 negatively regulates tumor cell growth and invasiveness whereas unphosphorylated EphA2 promotes these same behaviors in malignant cells. The association of EphA2 with malignancy is further detailed in international patent applications WO 01/12172 and WO 01/12804.

SUMMARY OF THE INVENTION

The present invention identifies low molecular weight protein tyrosine phosphatase (LMW-PTP) as a novel diagnostic and therapeutic target in cancer diagnosis, prognosis and treatment. Accordingly, the invention provides novel cancer diagnostic, prognostic and treatment methods.

In one aspect, the invention provides a method for the treatment of cancer in a mammal, preferably a human. In one embodiment of the treatment method of the invention, the method is useful for treating cancer in a mammal wherein the cancer cell expresses a low molecular weight protein tyrosine kinase (LMW-PTP). The treatment method involves administering to the mammal a treatment agent effective to inhibit the activity of LMW-PTP.

In another embodiment of the treatment method of the invention, the method is useful for treating cancer in a mammal wherein the cancer cell expresses a low molecular weight protein tyrosine kinase (LMW-PTP) and an EphA2 receptor molecule. The treatment method involves administering to the mammal a first treatment agent effective to inhibit the activity of LMW-PTP and a second treatment agent effective to favorably alter the biological activity of the EphA2 receptor molecule. Preferably, the biological activity of EphA2 is favorably altered by increasing the phosphotyrosine content of the EphA2 receptor molecule.

The cancer treated using the method of the invention is preferably a metastatic carcinoma. Optionally in the treatment method of the invention, the treatment agent is covalently linked to a cytotoxic agent.

Overexpression of LMW-PTP is indicative of the presence of cancer cells in the mammal. Thus, in another aspect, the invention provides a method for diagnosis of cancer in a mammal based upon overexpression of LMW-PTP. In one embodiment, the diagnostic method of the invention involves lysing cells in a biological material obtained from the mammal to yield a cell lysate; contacting the cell lysate with a diagnostic agent that binds LMW-PTP to form a bound complex; detecting the bound complex; and determining whether LMW-PTP is overexpressed in the biological sample relative to a noncancerous biological material. Optionally, the method also includes obtaining the biological material from the mammal. In another embodiment of the diagnostic method of the invention, expression levels of LMW-PTP are analyzed by assaying the biological material to determine whether LMW-PTP is overexpressed in the biological material relative to a noncancerous biological sample. This diagnostic method can be performed in the mammal or outside of the mammal. Any biological material of the mammal can be analyzed, for example a tissue, organ or fluid of the mammal.

In yet another aspect, the invention provides a screening method for evaluating the efficacy of a candidate cancer therapeutic agent that targets the EphA2 receptor molecule. In one embodiment, the screening method involves contacting a cancer cell expressing EphA2 receptor molecule and LMW-PTP with a candidate therapeutic agent to yield a treated cancer cell; determining the amount or activity of LMW-PTP in the treated cancer cell; and comparing the amount or activity of LMW-PTP in the treated cancer cell with the amount or activity of LMW-PTP in an analogous untreated cancer cell. A reduction in the amount or activity of LMW-PTP in the treated cell is indicative of the efficacy of EphA2 targeting of the candidate therapeutic agent.

BRIEF DESCRIPTION OF THE FIGURES

FIG. 10 shows that LMW-PTP overexpression alters two-dimensional morphology in transfected MCF-10A cells.

FIG. 15 shows a summary of immunofluorescence findings.

DETAILED DESCRIPTION OF THE PREFERRED EMBODIMENTS

Figure 1:
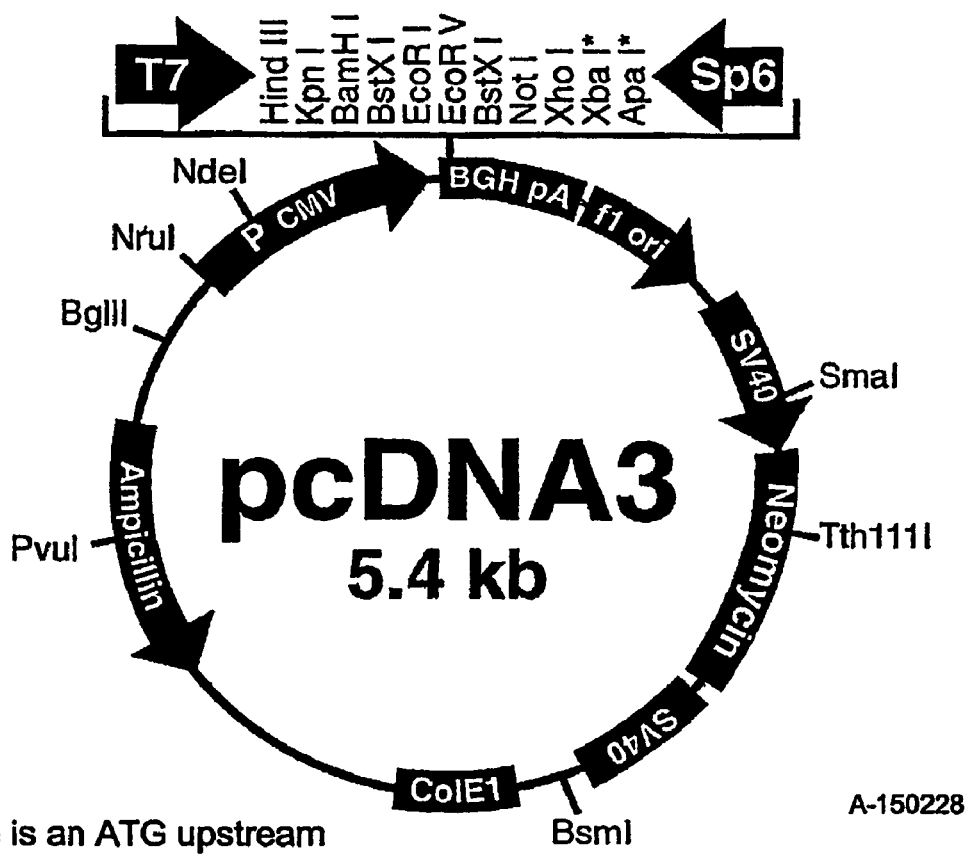
FIG. 1 shows a schematic map of the eukaryotic expression vector pcDNA3, a 5.4 kb mammalian expression vector. Unique restriction sites are indicated. The HPTP gene was cloned into the Hind III/BamH I sites of this vector. Expression of the gene was driven by the CMV promoter.

Tyrosine phosphorylation is controlled by cell membrane tyrosine kinases (i.e., enzymes that phosphorylate other proteins or peptides), and increased expression of tyrosine kinases is known to occur in metastatic cancer cells. We have made the surprising finding, however, that an enzyme that catalyzes the reverse reaction, dephosphorylation, is a powerful oncoprotein. This enzyme is low molecular weight protein tyrosine phosphatase (LMW-PTP), and its oncogenic potential is in at least some instances linked to the receptor tyrosine kinase EphA2, which is also implicated in oncogenesis and metastasis.

LMW-PTP is thus established as a new and unusual target for treatment methods directed to cancer therapy. LMW-PTP can be targeted either alone or in combination with treatments that target EphA2, other oncogenic tyrosine kinases, or other oncogenes or oncoproteins. LMW-PTP levels can also serve as a marker in cancer detection, or as a surrogate marker to analyze the impact of treatments that target EphA2 or other tyrosine kinases associated with the development or progression of cancer.

Low Molecular Weight Protein Tyrosine Phosphatase

Protein tyrosine phosphatases (sometimes also referred to phosphotyrosine phosphatases), known as PTPases, catalyze the hydrolysis of phosphomonoesters, specifically, the dephosphorylation of protein phosphotyrosyl residues. There are three major classes of PTPases: dual-specificity PTPases, high molecular weight PTPases and low molecular weight PTPases (Zhang, M., Stauffacher, C., and Van Etten, R. L. (1995), "The Three Dimensional Structure, Chemical Mechanism and Function of the Low Molecular Weight Protein Tyrosine Phosphatase," *Adv. Prot. Phosphatases* 9, 1-23). Several different acronyms are used interchangeably for low molecular weight (LMW) PTPase and include LMW-PTP, LMW PTP, LMW-PTPase and LMW PTPase.

LMW-PTPs represent a family of PTPases that includes members isolated from many different organisms. They typically have a relative molecular mass of about 18 kD. Members of the LMW-PTP family found in higher organisms include bovine (Heinrikson, R. L. (1969), "Purification and Characterization of a Low Molecular Weight Acid Phosphatase from Bovine Liver," *J. Biol. Chem.* 244, 299-307), *Erwinia* Burgert, P. and Geider, K. (1997), "Characterization of the ams I Gene Product as a Low Molecular Weight Acid Phosphatase Controlling Exopolysaccharide Synthesis of *Erwinia Amylovora*," *FEBS Lett.* 400, 252-256), budding yeast (Ltp1) (Ostanin, K., Pokalsky, C., Wang, S., and Van Etten, R. L. (1995), "Cloning and Characterization of a *Saccharomyces cerevisiae* Gene Encoding the Low Molecular Weight Protein-Tyrosine Phosphatase," *J. Biol. Chem.* 270, 18491-18499), fission yeast (Stp1) Mondesert, O., Moreno, S., and Russell, P. (1994), "Low Molecular Weight Protein Tyrosine Phosphatases are Highly Conserved Between Fission Yeast and Man," *J. Biol. Chem.* 269, 27996-27999), rat ACP1 and ACP2 isozymes (Manao, G., Pazzagli, L., Cirri, P., Caselli, A., Camici, G., Cappugi, G., Saeed, A., and Ramponi, G. (1992), "Rat Liver Low $M_r$ Phosphotyrosine Protein Phosphatase Isoenzymes: Purification and Amino Acid Sequences," *J. Prot. Chem.* 11, 333-345), human (HPTP) (Wo, Y.-Y. P., Zhou, M.-M., Stevis, P., Davis, J. P., Zhang, Z.-Y., and Van Etten, R. L. (1992), "Cloning, Expression, and Catalytic Mechanism of the Low Molecular Phosphotyrosyl Protein Phosphatase From Bovine Heart," *Biochemistry* 31, 1712-1721; Dissing, J. and Svensmark, O. (1990), "Human Red Cell Acid Phosphatase: Purification and Properties of the A, B, and C Isozymes," *Biochem. Biophys. Acta.* 1041, 232-242; Waheed, A., Laidler, P. M., Wo, Y.-Y. P., and Van Etten, R. L. (1988), "Purification and Physiochemical Characterization of a Human Placental Acid Phosphatase Possessing Phosphotyrosyl Protein Phosphatase Activity," Biochemistry 27, 4265-4273; Boivin, P. and Galand, C. (1986), "The Human Red Cell Acid Phosphatase Is a Phosphotyrosine Protein Phosphatase Which Dephosphorylates the Membrane Protein Band 3," *Biochem. Biophys. Res. Commun.* 134, 557-564), and BPTP (Zhang, Z-Y. and Van Etten, R. L. (1990), "Purification and Characterization of a Low-Molecular Weight Acid Phosphatase—A Phosphotyrosyl Protein Phosphatase from Bovine Heart," *Arch. Biochem. Biophys.* 282, 3949; Chernoff, J. and Li, H.-C. (1985), "A Major Phosphotyrosyl-Protein Phosphatase From Bovine Heart is Associated with a Low-Molecular-Weight Acid Phosphatase," *Arch. Biochem. Biophys.* 240, 135-145). These proteins, as well as other PTPases, share a common active site sequence motif, Cys-$(Xaa)_5$-Arg. Some proteins that share a high degree of sequence identity with the higher vertebrate enzymes include the low molecular weight PTPases from *Escherichia coli* (Stevenson, G. Andrianopopoulos, K. Hobbs, M., and Reeves, P. R. (1996), "Organization of the *Escherichia coli* K-12 Gene Cluster Responsible for Production of the Extracellular Polysaccharide Colanic Acid," *J. Bact.* 178, 4885-4893), *Klebsiella* (Arakawa, Y., Washarotayankun, R., Nagatsuka, T., Ito, H., Kato, N., and Ohta, M. (1995), "Genomic Organization of the *Klebsiella pneumoniae* CPS Region Responsible for Serotype K2 Capsular Polysaccharide Synthesis in the Virulent Strain Chedid," *J. Bacteriol.* 177, 1788-1796), *Synechococcus* (Wilbanks, S. M. and Glazer, A. N. (1993), "Rod Structure of a Phycoerythrin II-containing Phycobilisdome. I. Organization and Sequence of the Gene Cluster Encoding the Major Phycobilirotein Rod Components in the Genome of Marine *Synechococcus* sp. WH8020," *J. Biol. Chem.* 268, 1226-1234), and *Tritrichomonas foetus* (gb U66070).

Some mammalian low molecular weight PTPases exist as isozymes. Within specific species, the amino acid sequence identity between the isozymes is greater than 95%. One such species is human, where the human red cell protein tyrosine phosphatase (HPTP) is expressed. The two forms of this protein, A (fast) and B (slow), differ in their electrophoretic mobility when resolved during starch gel electrophoresis. Except for the variable region, residues 40-73, the isozymes have an identical amino acid sequence.

The human isozymes (A and B) have a high level of amino acid sequence identity when compared to BPTP, 81% and 94%, respectively. The crystal structure of BPTP, the prototype of low molecular weight PTPases, has been solved (Zhang, M., Van Etten, R. L., and Stauffacher, C. V. (1994), "Crystal Structure of Bovine Heart Phosphotyrosyl Phosphatase at 2.2-A Resolution," *Biochemistry* 33, 11097-11105). The structure consists of α-helices on both sides of a four-stranded central parallel β-sheet. This structure incorporates a portion of a Rossman fold, the classic nucleotide-binding fold consisting in part of two right-handed βαβ motifs. The crystal structure of HPTP-A and yeast LTP1 have been solved (Wang, S., Stauffacher, C. and Van Etten, R. L. (2000), "Structural and Mechanistic Basis for the Activation of a Low Molecular Weight Protein Tyrosine Phosphatase by Adenine," *Biochemistry* 39, 1234-1242; Zhang, M. (1995), Ph.D. Thesis, Purdue University), and resemble BPTP. Low molecular weight PTPases have eight conserved cysteines (all in free thiol form), seven conserved arginines, and two conserved histidines (Davis, J. P., Zhou, M. M., and Van Etten, R. L. (1994), "Kinetic and Site-Directed Mutagenesis Studies of the Cystein Residues of Bovine Low Molecular Weight Phosphotyrosyl Protein Phosphatase," *J. Biol. Chem.* 269, 8734-8740).

Tyrosine-phosphorylated proteins and peptides, as well as simpler molecules such as phosphotyrosine and pNPP, are all candidates for substrates of the low molecular weight PTPases.

Natural and synthetic inhibitors of these enzymes also exist. Among the strongest inhibitors of low molecular weight PTPases are the ions vanadate, tungstate, and molybdate.

EphA2 Receptor Tyrosine Kinase

EphA2, a 130 kD protein, is a member of the largest family of receptor tyrosine kinases (Andres, A. C., Reid, H. H., Zurcher, G., Blaschke, R. J., Albrecht, D., and Ziemiecki, A. (1994), "Expression of Two Novel eph-related Receptor Protein Tyrosine Kinases in Mammary Gland Development and Carcinogenesis," *Oncogene* 9, 1461-1467; Lindberg et al., *Mol. Cell. Biol.* 10:6316-6324 (1990)). It is expressed primarily in cells of epithelial cell origin such as breast, lung, ovary, colon, etc. This protein, also known as ECK, Myk2, and Sek2, was isolated from an erythropoietin-producing hepatocellular carcinoma cell line (Hirai, H., Maru, Y., Hagiwara, K., Nishida, J., and Takaku, F. (1987), "A Novel Putative Tyrosine Kinase Receptor Encoded by the Eph Gene," *Science* 238, 1717-1720). Due to multiple names and a growing family of different but related Eph proteins, a nomenclature committee met to officially name the proteins (Eph Nomenclature Committee (Flanaga, J. G., Gale, N. W., Hunter, T., Pasquale, E. B., and Tessier-Lavgne, M.) (1997), "Unified Nomenclature for Eph Family Receptors and Their Ligands, the Ephrins," *Cell* 90, 403-404). The proteins were named either EphA or EphB, depending on whether they bind ligands that are GPI-linked or transmembrane, respectively. EphA proteins bind ephrin-A ligands, whereas EphB proteins bind ephrin-B ligands. The number represents the order in which they were discovered.

Different methods have been used to isolate EphA2. First, hybridization techniques were used to isolate EphA2 from DNA libraries (Lindberg et al., *Mol. Cell. Biol.* 10:6316-6324 (1990); Hirai, H., Maru, Y., Hagiwara, K., Nishida, J., and Takaku, F. (1987), "A Novel Putative Tyrosine Kinase Receptor Encoded by the Eph Gene," *Science* 238, 1717-1720). Secondly, the polymerase chain reaction (PCR) was employed using primers for the kinase domain (Andres, A. C., Reid, H. H., Zurcher, G., Blaschke, R. J., Albrecht, D., and Ziemiecki, A. (1994), "Expression of Two Novel eph-related Receptor Protein Tyrosine Kinases in Mammary Gland Development and Carcinogenesis," *Oncogene* 9, 1461-1467; Gilardi-Hebenstreit, P., Nieto, M. A., Frain, M., Mattei, M. G., Chestier, A., Wilkinson, D. G., and Charnay, P. (1992), "An Eph-related Receptor Protein Tyrosine Kinase Gene Segmentally Expressed in the Developing Mouse Hindbrain," *Oncogene* 7, 1499-2506). Next, cDNA expression libraries were probed with antibodies specific for phosphotyrosine (Zhou, R., Copeland, T. D., Kromer, L. F., and Schulz, N. T. (1994), "Isolation and Characterization of Bsk, a Growth Receptor-like Tyrosine Kinase Associated with the Limbic System," *J. Neuro. Res.* 37, 129-143). Lastly, monoclonal antibodies were screened against proteins that are tyrosine phosphorylated in oncogenic transforming cells (Zantek, N. D. (1999), Ph.D. Thesis, Purdue University).

EphA2 binds ligands known as ephrinA, with the physiological ligand identified as EphrinA1. Ligand binding induces tyrosine phosphorylation of the Eph protein. EphA2, in particular, is able to bind five different ephrin ligands.

EphA2 has characteristic differences in normal and transformed breast epithelia (Zantek, N. D. (1999), Ph.D. Thesis, Purdue University). In normal breast epithelia, EphA2 is present in low protein levels, it is tyrosine phosphorylated, and, finally, it is localized in the sites of cell-cell adhesion. In transformed breast epithelia, high protein levels of EphA2 exist, it is no longer tyrosine phosphorylated, and it is localized in the membrane ruffles.

EphA2 has been found to have a functional role in cancer. When overexpressed, EphA2 is a powerful oncoprotein (Zelinski, D. P., Zantek, N. D., Stewart, J., Irizarry, A. & Kinch, M. S. (2001) *Cancer Res* 61, 2301-2306). Overexpression of EphA2 in MCF-10A cells causes malignant transformation. Also, injection of these overexpressing cells into nude mice causes tumors. Interestingly, the EphA2 in cancer cells and in EphA2-overexpressing cells is not tyrosine phosphorylated, whereas EphA2 in nontransformed cells is tyrosine phosphorylated.

LMW-PTP, shown herein to regulate EphA2, has also been shown to interact with another member of the Eph family, EphB1 (Stein, E., Lane, A. A., Cerretti, D. P., Schoecklmann, H. O., Schroff, A. D., Van Etten, R. L., and Daniel, T. O. (1998), "Eph Receptors Discriminate Specific Ligand Oligomers to Determine Alternative Signaling Complexes, Attachment, and Assembly Responses," *Genes & Dev.* 12, 667-678).

Therapeutic Inhibition of LMW-PTP Activity

Low-molecular weight protein tyrosine phosphatase (LMW-PTP) is overexpressed in a large number of tumor cells. The Examples below demonstrate that the phosphotyrosine content of EphA2 is negatively regulated by LMW-PTP, establishing a role for this phosphatase in oncogenesis. They further demonstrate that overexpression of LMW-PTP induces a concomitant increase in EphA2 levels and is sufficient to confer malignant transformation upon non-transformed epithelial cells. Oncogenesis that is associated with increased activation or expression of LMW-PTP (whether or not the cancer cells express EphA2) can be treated or prevented by inhibiting the activity of LMW-PTP in accordance with the invention.

These findings establish LMW-PTP as a target for prophylactic and therapeutic methods. By inhibiting the activity of LMW-PTP, dephosphorylation of EphA2 can be slowed or prevented, thereby favorably altering the activity of EphA2 and preventing or reversing cancer progression.

Treatments that result in an inhibition in the activity of LMW-PTP are therefore expected to be accompanied by a favorable change in the disease state of a cancer patient. Favorable changes in the disease state of a cancer patient include, for example, a reduction in the tumor burden, a slowing of tumor growth, prevention or deferral of disease stage progression and prevention or deferral of metastasis. Favorable changes in the disease state of a patient can be detected using any convenient method including radiography, sonography, biochemical assay, and the like.

The invention thus provides a method for treating cancer in a mammal, preferably a human. The method is also well-suited for veterinary applications such as treatment of cancer in a pet such as a cat or a dog. The method is effective to treat a cancer characterized by cells that overexpress LMW-PTP, particularly metastatic carcinoma cells of the breast, prostate, colon, lung, bladder, ovary, pancreas and skin (melanoma) that additionally possess overexpressed or functionally altered EphA2 tyrosine kinase receptor (see, e.g., Kinch et al., Clin. Cancer Res., 2003, 9(2):613-618; Kinch et al., Clin. Exp. Metastasis, 2003, 20(1):59-68; Walker-Daniels et al., Am J. Pathol., 2003, 162(4):1037-1042; Zelinski, D. P., Zantek, N. D., Stewart, J., Irizarry, A. & Kinch, M. S. (2001) *Cancer Res* 61, 2301-2306; Zantek, N. D. (1999), Ph.D. Thesis, Purdue University). A treatment agent that inhibits the biological activity of LMW-PTP is introduced into the mammal, either systemically or at the site of a cancer tumor, in an amount effective to inhibit the biological activity of EphA2. Optionally, the treatment agent can be linked to a drug, preferably a cytotoxic drug, thereby possessing the dual activities of inhibiting LMW-PTP and serving as a carrier molecule for the cytotoxic drug. Where the resulting molecular complex includes a cleavable therapeutic agent, treatment can include delivery of yet another agent to effect cleavage.

"Inhibition" in LMW-PTP activity can be assessed in comparison to LMW-PTP activity prior to treatment. Typically this is assessed in a laboratory setting using cell lines such as those described in the Examples below. Administration to a patient of a treatment agent that causes inhibition of LMW-PTP activity in a laboratory setting in model systems routinely used for human cancer research is fully expected to cause inhibition of LMW-PTP activity in the patent's cells in vivo. It should be understood that the method of the invention is not limited by the way in which, or the extent to which, LMW-PTP activity is inhibited in the target cells.

Methods for inhibiting LMW-PTP activity include, for example, those that act directly on the gene encoding one or more of the LMW-PTP enzymes (such as HPTP-A and HPTP-B), those that act on the mRNA transcript produced by the gene, those that interfere with the translation of the mRNA transcript into the protein, and those that directly impair the activity of the translated protein.

Transcription of a gene can be impeded by delivering to the cell an antisense DNA or RNA molecule or a double stranded RNA molecule. Examples include siRNA and iRNA. Another way the activity of an enzyme can be inhibited is by interfering with the mRNA transcription product of the gene. For example, a ribozyme (or a DNA vector operably encoding a ribozyme) can be delivered to the cell to cleave the target mRNA. Antisense nucleic acids and double stranded RNAs may also be used to interfere with translation.

The invention is not limited to the method used to deliver the treatment agent. When the treatment agent is a polypeptide, such as D129A LMW-PTP, it can be conveniently delivered in a gene therapy embodiment by introducing into the cell a DNA molecule operably encoding the treatment agent such that it is transcribed and translated once delivered to the cell. The DNA can be naked DNA or it can be provided as the part of a vector. The vector can be viral or nonviral (e.g., plasmid or cosmid), integrating or nonintegrating. Examples of viral vectors include retroviral vectors and adenoviral vectors.

Peptides, ligands, ligand mimics, peptidomimetic compounds and other small molecules are examples of those that can be used to directly compromise the activity of the translated protein. Optionally, these agents can be introduced using a delivery vehicle such as a liposome. Alternatively, a proteinaceous intracellular agent that inhibits the activity of LMW-PTP can be delivered as a nucleic acid, for example as RNA, DNA, or analogs or combinations thereof, using conventional methods, wherein the therapeutic polypeptide is encoded by the nucleic acid and operably linked to regulatory elements such that it is expressed in the target mammalian cell.

Preferred treatment agents for use in inhibiting LMW-PTP activity include small molecules, peptides, antisense oligonucleotides, and substrate mimics (e.g., non-hydrolyzable or substrate trapping inhibitors). Treatment agents can include antagonists that resemble substrate or that interfere with the binding of LMW-PTP to its substrate, particularly those that interfere with EphA2-LMW-PTP interactions. Small molecules that resemble pyridoxyl phosphate are particularly preferred, such as those that substitute phosphonic acid or sulfonic acid for the phosphate group in pyridoxal phosphate. The active site of LMW-PTP can be targeted, particularly Tyr131, Tyr132 and Asp129. For example, as shown in the examples below, the substrate-trapping mutant LMW-PTP protein D129A (Asp to Ala at position 129) effectively competes against wild-type LMW-PTP to restore normal epithelial morphology to transformed cells. Because the BPTP x-ray crystal structure has been solved, rational drug design can be used to identify or design highly specific inhibitors of LMW-PTP which are expected to be especially useful therapeutically.

A preferred embodiment of the treatment method includes administration to cancer patient of a first treatment agent that targets LMW-PTP and a second treatment agent that targets EphA2. The treatment agents may be administered in any order or may be administered simultaneously (co-administration). Multiple treatment agents that target LMW-PTP or EphA2 may be administered.

The treatment agent that targets EphA2 can be, for example, an antibody, a small molecule, a peptide, a ligand or ligand mimic, or an antisense nucleic acid. In one aspect of the method, the second treatment agent "activates" EphA2 by binding to an extracellular epitope on the receptor molecule. Ligand-mediated activation is characterized by increased EphA2 phosphotyrosine content and is accompanied by a favorable alteration in EphA2 activity. A "favorable alteration in EphA2 activity" means a change in the activity, number (i.e., protein levels) and/or function of EphA2 receptors in cancer cells so as to arrest or reverse cell growth or proliferation, or to initiate or cause killing of the cancer cell. Arrest or reversal of cell growth or proliferation can be evidenced by various phenotypic changes in the cancer cells such as increased differentiation, decreased affinity for ECM proteins, increased cell-cell adhesions, slower growth rate, reduced numbers of EphA2 and/or increased localization of EphA2, decreased cell migration or invasion, and can be caused either directly or indirectly. Optionally, the second treatment agent causes EphA2 crosslinking, and/or and acceleration in the degradation of EphA2. In another aspect of the invention, the second treatment agent reduces expression of EphA2 in a target cancer or precancerous cell at the DNA/RNA level, for example via the binding of an antisense oligonucleotide.

Detection of Cancer or Precancerous Conditions

LMW-PTP can also serve as a marker for cancer or precancerous conditions in a mammal, preferably a human. The invention therefore also includes a method for diagnosing a cancerous or precancerous condition, or staging a cancer, by detecting and, optionally, quantifying the amount or activity of LMW-PTP in a biological sample. The diagnostic method of the invention can be used to obtain or confirm an initial diagnosis of cancer, or to provide information on cancer localization, cancer metastasis, or cancer prognosis. The method is applicable to both human and veterinary medical uses.

In one embodiment of the diagnostic method, a biological sample such as a tissue, organ or fluid that has been obtained from the mammal is analyzed. The method optionally includes the step of removing the biological material from the mammal. Cells present in the biological material are lysed, and the lysate is contacted with a polyclonal or monoclonal LMW-PTP antibody. The resulting antibody/LMW-PTP bound complex is either itself detectable or capable of associating with another compound to form a detectable complex. Bound antibody can be detected directly in an ELISA or similar assay; alternatively, the diagnostic agent can comprise a detectable label, and the detectable label can be detected using methods known in the art.

In embodiments of the diagnostic method wherein LMW-PTP is detected via the binding of a detectably labeled diagnostic agent such as an antibody, preferred labels include chromogenic dyes, fluorescent labels and radioactive labels. Among the most commonly used chromagens are 3-amino-9-ethylcarbazole (AEC) and 3,3'-diaminobenzidine tetrahydrocholoride (DAB). These can be detected using light microscopy.

The most commonly used fluorescent labeling compounds are fluorescein isothiocyanate, rhodamine, phycoerythrin, phycocyanin, allophycocyanin, o-phthaldehyde and fluorescamine. Chemiluminescent and bioluminescent compounds such as luminol, isoluminol, theromatic acridinium ester, imidazole, acridinium salt, oxalate ester, luciferin, luciferase, and aequorin also may be used. When the fluorescent-labeled antibody is exposed to light of the proper wavelength, its presence can be detected due to its fluorescence.

Radioactive isotopes which are particularly useful for labeling the antibodies of the present invention include $^{3}H$, $^{125}I$, $^{131}I$, $^{35}S$, $^{32}P$, and $^{14}C$. The radioactive isotope can be detected by such means as the use of a gamma counter, a scintillation counter, or by autoradiography.

Antibody-antigen complexes can be detected using western blotting, dot blotting, precipitation, agglutination, enzyme immunoassay (EIA) or enzyme-linked immunosorbent assay (ELISA), immunohistochemistry, in situ hybridization, flow cytometry on a variety of tissues or bodily fluids, and a variety of sandwich assays. These techniques are well known in the art. See, for example, U.S. Pat. No. 5,876,949, hereby incorporated by reference. In an enzyme immunoassay (EIA) or enzyme-linked immunosorbent assay (ELISA), the enzyme, when subsequently exposed to its substrate, reacts with the substrate and generates a chemical moiety which can be detected, for example, by spectrophotometric, fluorometric, or visual means. Enzymes which can be used to detectably label antibodies include, but are not limited to malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase, and acetylcholinesterase. Other methods of labeling and detecting antibodies are known in the art and are within the scope of this invention.

In another embodiment of the diagnostic method, a biological material is assayed for LMW-PTP phosphatase activity. Depending on the assay used, this method can be performed on biological material that is present in the mammal or that has been removed from the mammal. For example, biological material obtained from the mammal can be subjected to a biochemical assay for LMW-PTP phosphatase activity. Detection can also be accomplished by employing a detectable reagent that binds to DNA or RNA coding for the LMW-PTP protein.

LMW-PTP can be used as a marker for cancer, precancerous or metastatic disease in a wide variety of tissue samples, including biopsied tumor tissue and a variety of body fluid samples, such as blood, plasma, spinal fluid, saliva, and urine.

Other antibodies may be used in combination with antibodies that bind to LMW-PTP to provide further information concerning the presence or absence of cancer and the state of the disease. For example, the use of anti-EphA2 or phosphotyrosine-specific antibodies provides additional data for determining detecting or evaluating malignancies.

LMW-PTP Activity as an Indicator of the Efficacy of Cancer Treatments

LMW-PTP can serve as a surrogate marker to evaluate the efficacy of cancer therapeutic agents, particularly those that target EphA2. The amount or activity of LMW-PTP in a cancer cell that overexpresses LMW-PTP (the control) is compared to the amount or activity of LMW-PTP in an analogous cancer cell that has been treated with a candidate therapeutic agent. Reduction in the amount or activity of LMW-PTP in the treated cell is indicative of an efficacious cancer treatment.

The present invention is illustrated by the following examples. It is to be understood that the particular examples, materials, amounts, and procedures are to be interpreted broadly in accordance with the scope and spirit of the invention as set forth herein.

EXAMPLES

Example I

Protein-Protein Interactions Involving Low Molecular Weight Protein Tyrosine Phosphatase and EphA2

Materials and Methods

Protein Production. Ampicillin, N-Z-amine A (casein hydrolysate), IPTG, and SP-Sephadex C-50 all were obtained from Sigma. The SP-Sephadex G-50 was purchased from Pharmacia The YM3 membranes were from Amicon. All other materials were purchased either from Sigma or BioRad.

Cell lines. The cell models used for this study were breast epithelia. A commonly used cell line in this research laboratory is MCF-10A. This cell line is a part of the family of MCF-10 cells, an established immortal human mammary epithelial cell line. MCF-10 cells were isolated from the mammary tissue of an adult woman who had fibrocystic disease. MCF-10A cells grow as attached cells. The MCF-10A (Neo) cell line is the parent cell line, MCF-10A, with a neomycin resistance gene. The MDA-MB-231 cell line is a highly invasive and metastatic mammary cell line. These cells were isolated from an adult woman with breast cancer.

Care for these cells consist of handling them every two days, either by refreshing the media or splitting them. To split the cells, the media was first removed by aspiration. The cells were washed in 2-3 ml PBS, then trypsin solution (2-3 ml diluted 1:50 in PBS) was added and the plates were placed in the incubator at 37° C. for 10-30 minutes. Next, 2-3 ml of media was added to each plate. The cells in the PBS/trypsin solution and media were spun to a pellet in a tabletop centrifuge for 5 minutes. The PBS/trypsin solution and media were aspirated, and the cells were resuspended in media The cells were then plated in the tissue culture dishes.

The growth medium for the MCF-10A (Neo) cells consists of DMEM/F12, 5.6% horse serum, 20 ng/ml epidermal growth factor, all from Upstate Biotechnology, Inc., 100 µg/ml streptomycin, 100 units/ml penicillin, 10 µg/ml insulin from Sigma, 0.25 µg/ml fungizone, and 2 nM L-Glutamine. The growth medium for the MDA-MB-231 cells consists of RPMI, 2 nM L-Glutamine, 100 µg/ml streptomycin, and 100 units/ml penicillin.

Antibodies. An antibody that recognizes the intracellular domain of EphA2 is D7 (Upstate Biochemicals, New York). This monoclonal antibody (MAb) was produced from a bulk culture as stated in Zantek, Ph.D. Thesis, Purdue University, 1999. For immunoprecipitations with this antibody, 30 µl were used. For immunoblotting, a dilution of 1:1 in TBSTB (30 ml 5M NaCl, 50 ml 1 M Tris, pH 7.6, 1 ml Tween-20, 1 g BSA, and 920 ml ddH$_2$O) was used. For immunofluorescence microscopy, the antibody was used without dilution.

The monoclonal antibodies directed against HPTP (10.1 and 7.1) were developed as stated in Alfred Schroff, Ph.D. Thesis, Purdue University, 1997. For immunoprecipitations, with 10.1 (α-HPTP-B) 10 µl were used. For immunoblotting, the antibody was diluted in TBSTB at 1:100. For immunofluorescence microscopy, the antibody was diluted at 1:10 in PBS. The same conditions were used for the other MAb directed against HPTP, 7.1 (α-HPTP-A/B). For the polyclonal antibodies against HPTP, 10 µl of antibody were used for immunoprecipitation. For immunoblotting, the antibody was diluted in TBSTB at 1:2000. For immunofluorescence microscopy, the antibody was diluted in PBS at 1:100.

To detect phosphotyrosine, the antibody known as 4G10 was used. This antibody was produced from a bulk culture. For immunoblotting, a dilution of 1:1 in TBSTB was used. The secondary antibodies used for immunofluorescence microscopy were DAR-Fl at a 1:40 dilution and/or DAM-Rh at a 1:100 dilution in PBS. For immunoblotting experiments, either Goat Anti-Mouse (for MAb) or Goat Anti-Rabbit (for PAb) was used at a 1:10,000 dilution in TBSTB.

Affinity matrices. Protein-A Sepharose was purchased from Sigma. The Affi-gel 10 was purchased from BioRad.

Other materials. Other materials were purchased from Fisher, Pierce, Malinckrodt, New England Biolabs, QIAGEN, and Roche Diagnostics.

LMW-PTP expression and purification. The growth medium (M9ZB) was prepared as follows: in a 4 L flask, 20 g N-Z-amine A (casein hydrolysate), 10 g NaCl, 2 g NH$_4$Cl, 6 g KH$_2$PO$_4$, and 12 g Na$_2$HPO$_4$H$_2$O were dissolved in 2 L of ddH$_2$O. The pH of the medium was then adjusted to 7.4 with NaOH pellets. To a 500-ml flask, 200 ml of M9ZB solution were poured. The two containers of media were then autoclaved for 20 minutes. After cooling to room temperature, filter sterilized solutions of 20 mL 40% glucose and 2 mL 1M MgSO$_4$ were added per 2 L of medium. Just prior to inoculation 200 µl of 50 mg/mL Amp was added to the flask containing 200 ml (M9ZB) medium. A 200-ml culture of the BL21 strain of *E. coli* containing the recombinant plasmid with the gene of interest was grown overnight on a gyratory shaker set at 250-300 rpm at 37° C.

The next day, 1.8 ml of 50 mg/mL Amp was added to the remaining 1.8 L of fresh medium. The overnight culture was then diluted 1:10 in the fresh (M9ZB) medium, and the cells were allowed to grow an additional 3 hours. When the optical density at 600 nm (OD$_{600}$) reached between 0.6 and 1.0, 2 ml of 4 mM IPTG were added to induce protein expression. The culture was incubated at 37° C. for an additional 3 hours for WT-PTPase or 6 hours for mutant PTPases. The cells were harvested by refrigerated centrifugation for 15 minutes at 5000 rpm. The supernatant was poured back into the 4-L flask, then autoclaved for 20 minutes before discarding. The cell pellet was resuspended and washed in 10 mL 0.85% NaCl, spun to a pellet again at 500 rpm, then resuspended in 2 mL 0.85% NaCl. The mixture was placed in a small centrifuge tube then spun at 5000 rpm for 10 minutes. The supernatant was poured off, and the pellet was either stored at −20° C. overnight or lysed immediately.

The cell pellet was thawed (if applicable) then resuspended in 100 mM CH$_3$COONa buffer, pH 5.0, containing 1 mM EDTA and 1 mM DTT. The DTT was added just prior to use. The cells were disrupted by passing them twice through a pre-chilled French pressure cell set at a pressure gauge of 1000 psi. The lysates were spun to a pellet in the refrigerated centrifuge at 16,000 rpm for 15 minutes. The supernatant was poured into a new centrifuge tube, then loaded onto an SP-Sephadex C-50 cation-exchange column (1.5×30 cm) that was pre-equilibrated with 10 mM CH$_3$COONa buffer, pH 4.8, containing 30 mM NaH$_2$PO$_4$, 1 mM EDTA and 60 mM NaCl.

The C-50 column was washed with 10 bed-volumes of 10 mM CH$_3$COONa buffer until the A$_{280}$ was roughly zero. The protein was then eluted with a high salt solution, 300 mM NaH$_2$PO$_4$ and 1 mM EDTA at pH 5.1. The flow-rate was set at 30-40 mL/hr. Each fraction collected contained approximately 6 ml. The fractions with the highest A$_{280}$ were resolved on a 15% SDS-polyacrylamide gel to access protein purity. The purest fractions were combined, then concentrated to roughly 5 ml using an Amicon ultrafiltration apparatus. The concentrate was loaded on a Sephadex G-50 size exclusion column that was pre-equilibrated with 10 mM CH$_3$COONa buffer at pH 4.8, containing 30 mM NaH$_2$PO$_4$, 1 mM EDTA and 60 mM NaCl. The flow-rate was set at 15-25 ml/hr and fractions of approximately 6 mL were collected. The fractions with the highest A$_{280}$ were tested on a 15% SDS-polyacrylamide gel to assess protein purity. The purest fractions were combined and stored at 4° C. in G-50 buffer.

Immunofluorescence microscopy. Up to five glass coverslips were placed in a 3.5 cm dish. The cell line(s) appropriate for the particular study was plated into those dishes 24 hours prior to use. The cells usually reached a confluence of 60-70% by this time. The cells were fixed in a 3.7% formaldehyde solution for 2 minutes, then permeabilized in 1% Triton for 5 minutes, and washed in Universal Buffer (UB) for 5 minutes. The cells were then incubated at room temperature with the primary antibody for 30 minutes. Next, the cells were washed in UB (12 ml 5 M NaCl, 20 ml 1 M Tris, pH 7.6, 4 ml 10% Azide) for 5 minutes. The cells were then incubated with a secondary antibody for 30 minutes. After a brief wash for 5 seconds in ddH$_2$O, the coverslips were placed face down on approximately 5 µl of FluorSave (Calbiochem) on a glass slide. The cells were allowed to dry at room temperature for approximately 15 minutes; then they were placed under a hair dryer set on "low" for an additional 15 minutes or until dry. The cells were viewed under an oil immersion lens (60×) of a fluorescence microscope.

Immunoprecipitation. For immunoprecipitations (IPs) with monoclonal antibodies, Rabbit Anti-Mouse Protein-A Sepharose (RAMPAS) was used. For those with polyclonal antibodies, Protein-A Sepharose (PAS) was used. The beads were prepared by, first, adding Protein-A Sepharose to the 100 µl-mark of a 1.5 mL microfuge tube. Next, 1 ml of UB was added to swell the beads. For RAMPAS, 50 µl/ml Rabbit Anti-Mouse (RAM) IgG was also added to the tube of beads and UB. The mixture(s) were allowed to rotate on a rotary stirrer overnight at 4° C. The next day, the beads were washed three times in 1 ml of UB. The beads were then brought to a 50% slurry in UB.

The plate of cells was placed on ice. The cells were washed once with 2-3 ml of PBS. Afterwards, the cells lysed in a 1% Triton lysis buffer (5 ml 1 M Tris, pH 7.6, 3 ml 5 M NaCl, 1 ml 10% NaN$_3$, 1 ml 200 mM EDTA, 10 ml 10% Triton X-100, 80 ml ddH$_2$O) or RIPA lysis buffer (5 ml 1M Tris, pH 7.6, 3 ml 5 M NaCl, 1 ml 10%, NaN$_3$, 1 ml 200 mM EDTA, 10 ml 10% Triton X-100, 5 ml 10% deoxycholate, 500 µl 20% SDS, 74.5 ml ddH$_2$O) lysis buffer containing 1 mM Na$_3$VO$_4$, 10

μg/ml leupeptin, and 10 μg/ml aprotinin for 5 minutes on ice. The lysates were collected, and each set of lysates was normalized for equal protein content using Coomassie Protein Assay Reagent. A plate-reader was used to measure the absorbance of 590 nm. After equalizing the lysates with the appropriate lysis buffer, the samples were prepared.

For each sample, 30 μl PAS (or RAMPAS) was added to each sample tube. Next, the appropriate primary antibody was added. Finally, 150-200 μl portions of the lysates were added. The samples were allowed to rotate at 4° C. for either 1.5 hours or overnight. The samples were then washed three times in 1 ml of the same lysis buffer that had been used to lyse the cells. After the final wash, 15 μl Laemmli buffer was added to the pelleted beads, and the samples were boiled for 10 minutes. Afterwards, the samples were loaded and resolved on a 15% SDS-polyacrylamide gel set at 220 V for 1.75 hours. After protein resolution, the proteins were transferred to nitrocellulose overnight.

Substrate trapping. Purified, catalytically-inactive LMW-PTP recombinant mutants, D129A-BPTP and C12A-BPTP, were used to create potential substrate trap(s). The affinity support was prepared by, first, washing 1-1.5 ml of Affi-gel 10 in several volumes of cold ddH$_2$O. Next, the moist gel was added to a 15-ml conical tube, along with a 5 mg/ml of pure PTPase mutant. The tube was rotated at 4° C. for 4 hours to allow the protein to couple to the beads. Afterwards, 100 μl ethanolamine per 1 ml Affi-gel was added to block reactive gel sites that had not been bound by protein, then the tube was rotated for an additional hour. The slurry was poured into a small plastic column. The beads were allowed to settle in the column, they were then washed with 20 ml of ddH$_2$O. The pH of the wash was measured. If greater than or equal to seven, the pH was adjusted with 10 mM HCl. Next, the A$_{280}$ was measured. If not near zero, the washes were continued until the A$_{280}$ read near zero. The column was stored at 4° C. until used.

Prior to application of the lysates, the column was washed in 10 ml of ddH$_2$O three times, then equilibrated in the appropriate lysis buffer. The cells were lysed in the appropriate lysis buffer for 5 minutes on ice. The lysates were collected and added to the column to incubate for various times at 4° C. The beads were then washed in the appropriate lysis buffer three times. Laemmli buffer was added to the beads, which were boiled for 10 minutes. The samples were resolved on a 15% SDS-polyacrylamide gel, and finally transferred to nitrocellulose overnight.

Dephosphorylation. MCF-10A (Neo) cells were grown to 80% confluence. The cells were lysed in 1% Triton lysis buffer for 5 minutes on ice. The lysates were collected and combined. EphA2 IPs were prepared: 30 μl D7, 30 μl RAMPAS, and 200 μl lysates. The IPs were mixed for 1.5 hours at 4° C. They were washed two times in 500 μl Triton lysis buffer, then twice in 500 μl of ddH$_2$O. Each pellet was resuspended in 10 mM 50 μl CH$_3$COONa buffer, and the tubes were placed in a 37° C. waterbath for 5 minutes to adjust the temperature to physiological conditions. Next, 500 μl of PTPase solution at the chosen concentration, was added to the tubes to react with EphA2 for the chosen times. At the end of the reaction, the beads were pelleted and the supernatant was removed by aspiration. Laemmli buffer was added to each sample and they were boiled for 10 minutes. Finally, the proteins were separated on a 10% SDS-polyacrylamide gel, and transferred to nitrocellulose overnight.

Immunoblotting. The nitrocellulose membrane was stained with Ponceau S to identify and mark the location of the molecular weight markers. The membrane was rinsed several times in ddH$_2$O to remove the dye. Non-specific sites on the membrane were blocked with a solution of Teleostean gelatin (50 ml of TBSTB and enough gelatin to give a "tea" color). The membrane was incubated in the blocking solution at room temperature for 30 minutes. Next, the membrane was incubated with primary antibody for 30 minutes. The membrane was washed three times for 10 minutes each in TBSTB, which was followed by a 30-minute incubation with secondary antibody. Afterwards, the membrane was washed three times for 8 minutes each in TBSTB, then twice for 6 minutes each in TBS (30 ml 5 M NaCl, 50 ml 1 M Tris, pH 7.6, 920 ml ddH$_2$O). Next, the chemiluminescent reagents were added to the membrane (1:1). Finally, the film was exposed to the membrane, which was wrapped in Saran Wrap, and developed.

Small-scale DNA purification. The plasmid pET-11d containing the gene for HPTP, was purified from the BL21 strain of E. coli using the commercially available QIAprep Miniprep from QIAGEN. E. coli containing HPTP-A and HPTP-B were both, but separately, streaked onto LB/Amp plates. Both plates were placed in a 37° C. incubator overnight. The next day, 3 ml of LB medium and 6 μl Amp were placed into two sterile snap-top tubes. The tubes were then labeled HPTP-A or HPTP-B. One colony from each plate was used to inoculate the respectively labeled tube with a colony containing the HPTP-A gene or the HPTP-B gene. The tubes were placed on a shaker set at 250 rpm overnight (12-16 hours). The next day, the cultures were spun to a pellet, and the supernatant was removed by aspiration.

To purify the DNA from bacterial pellets using the QIAprep Miniprep protocol, the bacterial pellets were resuspended in 250 μl of a buffered RNase A solution (Buffer P1). Next, the cell suspension was placed in a microfuge tube and lysed in 2501 μl of an alkaline lysis buffer (Buffer P2) consisting of NaOH and SDS. The tubes were inverted gently five times. Lysis was carried out for 5 minutes. The mixture was then neutralized by adding 350 μl neutralizing buffer (Buffer N3).

After spinning the tubes at 13,000 rpm for 10 minutes, the supernatant was transferred to the QIAprep spin column. The spin column was placed in a 2-ml collection tube. Together, they were placed in a centrifuge and spun at 13,000 rpm for 1 minute. The flow-through was discarded. Next, the spin column was washed with 750 μl of Buffer PE, and spun at 13,000 rpm for 1 minute. After discarding the flow-through, the spin column was spun once more at 13,000 rpm for 1 minute. The spin column was placed in a clean microfuge tube, and the DNA was eluted with 601 μl of Buffer EB and stored at −20° C.

Amplification of the coding regions. Polymerase chain reaction was used to amplify the coding regions of the genes. The primer designed for the forward strand contains a Hind III restriction site: AAT TTA AAG CTT CCA TGG CGG AAC AGG CTA CCA AG (SEQ ID NO:1). The primer designed for the reverse strand contains an EcoR I restriction site: CGT TCT TGG AGA AGG CCC ACT GAG AAT TCT TCG T (SEQ ID NO:2). An additional primer designed for the reverse strand contains a BamH I restriction site: GCG CGC GGA TCC TCA GTG GGC CTT CTC C (SEQ ID NO:3).

Briefly, 50 μl reaction mixtures consisting of 40 μl ddH$_2$O, 5 μl 10x buffer, 1 μl forward primer, 1 μl reverse primer, 1 μl dNTPs and 1 μl pfu polymerase were prepared. The reaction mixtures were placed in a thermal cycler set for the following cycle: 94° C. for 2 minutes, 94° C. for 1 minute, 55° C. for 1 minute, 65° C. for 1 minute, 65° C. for 10 minutes, then hold at 4° C. Steps two through four were repeated 30 times prior to proceeding to the next step, 65° C. for 10 minutes.

At the end of the cycle, the PCR products were analyzed on a 1% agarose gel (600 mg agarose, 1.2 ml 50×TAE, 58.8 ml ddH$_2$O). The PCR products were then purified using the commercially available QIAquick PCR purification kit from QIAGEN. Briefly, five volumes of Buffer PB were added to one volume of the PCR product reaction mixture and mixed briefly. The mixture was added to the QIAquick spin column and spun for 1 minute at 13,000 rpm. After discarding the flow-through, 750 μl of PE Buffer was added to the column and spun for 1 minute more at 13,000 rpm. The column was placed in a clean microfuge tube, and 30 μl of Buffer EB was added to the column. The column incubated at room temperature with the buffer for 1 minute before being spun at 13,000 rpm for 1 minute to elute the DNA.

Removal of the extensions. The PCR product reaction mixtures were prepared for digestion: 5 μl PCR product, 1 μl NEB-Buffer 2, 1 μl 10×BSA, and 0.9 μl Hind III/BamH I stock. The Hind III/BamH I stock consisted of 2.4 μl Hind III and 1.2 μl Bam H I. The reaction mixture for digestion for the pcDNA3 vector (FIG. 1) from Invitrogen was prepared: 1 μl pcDNA3, 1.5 μl NEB-Buffer 2, 1.5 μl 10×BSA, 0.5 μl Hind III, and 0.5 μl BamH I. The plasmid pcDNA3 is a 5.4 kb mammalian expression vector. The HPTP gene was cloned into the Hind III/BamH I sites of this vector, and expression of the gene was driven by the CMV promoter. The PCR products and the mammalian expression vector, pcDNA3, were digested at 37° C. for 2.5 hours. The digests were analyzed on a 1% agarose gel. After resolution, a photograph was taken of the gel. Digestion of the PCR products and the pcDNA3 vector were expected to generate fragments that were 491 bp and 5,428 bp, respectively.

Gel pieces containing the digested products were removed from the gel and placed in a microfuge tube. To remove the digested products from the gel, a commercially available QIAquick Gel Extraction kit from QIAGEN was used. Briefly, 210 μl of Buffer QG were added to the tubes. The tubes were placed in a 50° C. waterbath for approximately 10 minutes, with mixing every 2-3 minutes. Next, 70 μl of isopropanol were added to the tubes and mixed. The samples were then placed in a column attached to a collection tube and spun at 13,000 rpm for 1 minute. After discarding the flow-through, 500 μl of Buffer QG were added to the column, and the column was spun for 1 minute at 13,000 rpm. The flow-through was discarded, and the column was washed with 750 μl of Buffer PE then spun at 13,000 rpm for 1 minute. The flow-through was discarded, and the column was spun once more at 13,000 rpm for 1 minute to elute the DNA. The DNA was stored at −20° C.

Ligation and transformation. The amplified HPTP-A and HPTP-B genes were both, but separately, ligated with the pcDNA3 vector. The ligation reaction mixture was prepared: 10 μl insert, 5 μl vector, 2 μl 10× ligation buffer, 2 μl 10×ATP, and 1 μl ligase. The ligation mixtures were placed in a thermal cycler set at 16° C. for 18 hours followed by holding the temperature at 4° C.

The DH5α strain of competent *E. coli* was transformed with the ligation mixtures. Two microfuge tubes each with 200 μl of competent *E. coli* (DH5α) were thawed on ice. The ligation mixture was added to each tube of cells, the tubes were vortexed briefly, and then incubated on ice for 20 minutes. The tubes were placed in a 42° C. waterbath for 1.5 minutes, then placed on ice for 2 minutes. The contents of the tubes were placed separately into tubes containing 1 ml of LB. The mixtures were placed on the shaker set at 250 rpm for 45 minutes. Next, 200 μl of each culture were spread onto two LB/Amp plates. The plates were placed in the 37° C. incubator lid side up for 10 minutes, then lid side down overnight (16-18 hours).

Screen of colonies. The QIAprep Miniprep protocol was used to purify the DNA from each of the six bacterial cultures. Tubes containing the purified DNA were labeled appropriately: colony A1, colony A2, colony B1, colony B2, etc. To screen the colonies, purified DNA from each was digested with Hind III and BamH I; Nde I and EcoR I; and Acc I. The Hind III/BamH I digestion reactions were prepared: 5 μl vector/insert, 1 μl NEB-Buffer 2, 1 μl 10×BSA, 1.8 μl Hind III/BamH I stock, 6.2 μl ddH$_2$O. The Hind III/BamH I stock was prepared as follows: 7.2 μl BamH I added to 9.6 μl Hind III. Next, the Nde I/EcoR I digestion reactions were prepared: 5 μl vector/insert, 0.5 μl EcoR I, 0.3 μl Nde I, 1.5 μl NEB-Buffer 4, 7.7 μl ddH$_2$O. Finally, the Acc I digestion reactions were prepared: 5 μl vector/insert, 0.5 μl Acc I, 1.5 μl NEB-Buffer 3, and 8 μl ddH$_2$O. All digests were done overnight at 37° C. The digests were resolved on a 1% agarose gel and a photograph was taken of the gel.

Medium-scale DNA purification. A six-hour 5 ml culture grew at 37° C. on the shaker set at 250 rpm. The 5-ml culture was diluted with 50 ml of LB. The tube was placed on the shaker overnight. On the next day, 40 ml of the overnight culture was transferred to a 5-ml screw-cap centrifuge tube and pelleted by centrifugation for 5 minutes at 5000 rpm. The commercially available QUANTUM MidiPrep from BioRad was used to purify DNA on a medium scale. Briefly, the supernatant was poured off and 5 ml of Cell Resuspension solution were added to the cell pellet. The tube was vortexed to resuspend the cells. Next, 5 ml of Cell Lysis solution were added to the tube, then inverted six to eight times. The mixture was neutralized by adding 5 ml Neutralization solution, followed by inverting the tube six to eight times, neutralized the solution. The mixture was spun for 10 minutes at 8000 rpm. The supernatant was transferred to a new tube along with 1 ml of Quantum-Prep matrix. The mixture was gently swirled for 15 to 30 seconds, then spun for 2 minutes at 8000 rpm. The supernatant was poured off, then 10 ml of wash buffer were added to the matrix and mixed by shaking. The tube was spun for 2 minutes at 8000 rpm. After pouring the wash buffer from the pellet, 600 μl Wash Buffer were added to the tube to resuspend the pellet. The spin column was attached to a microfuge tube and a hole was punctured in the lid of the microfuge tube. After spinning the tube for 30 seconds at 12,000 rpm, the flow-through was discarded. Next, 500 μl of Wash Buffer was added to the tube, and the tube was spun for 30 seconds at 12,000 rpm. The flow-through was discarded, then the column was spun for 2 minutes more at 12,000 rpm to remove residual Wash Buffer. The column was transferred to a clean microfuge tube. The DNA was eluted with 600 μl of TE (pH 8).

Next, the DNA was ethanol-precipitated by adding 1/10 the volume of 5 M NaCl following by two times that total volume (NaCl plus DNA) of 100% ethanol. The microfuge tube was gently inverted a few times and incubated at −20° C. for 20 minutes. The DNA was spun to a pellet for 10 minutes at 13,000 rpm. Under sterile conditions, the ethanol/NaCl was aspirated from the pellet. The pellet was left to air dry in the hood. Afterwards, the DNA was resuspended in 100 μl sterile TE (pH 8). To determine the concentration of the DNA sample, the absorbance at 260 nm ($A_{260}$) was measured. The DNA was stored at −20° C.

Transfection. To overexpress HPTP in the MCF-10A (Neo) cell line, the commercially available FuGENE® transfection kit from Roche Diagnostics was used. The cells were plated 18 hours prior to use in 6-well plates such that their confluence would be approximately 50% on the day of transfection. In a microfuge tube, 97 μl serum-free dilution media was added to 3 μl of the FuGENE reagent. The diluted FuGENE was incubated at room temperature for 5 minutes. Next, 1 μg of DNA was added to a second microfuge tube. Dropwise, the diluted FuGENE reagent was added to the DNA. The tube was gently tapped to mix the contents of the tube. The tube was then incubated for 15 minutes at room temperature. The media on the cells was replaced with 2 ml of fresh media. Dropwise, the FuGENE/media solution was added to the plated cells, then the plate was swirled to distribute the contents around the plate. The cells were incubated at 37° C. for 36 to 48 hours.

On the day of analysis, the cells were lysed in 1% Triton lysis buffer, HPTP and D7 immunoprecipitations were done. The samples were eventually resolved on a 15% SDS-polyacrylamide gel, then transferred to nitrocellulose overnight. The next day, immunoblotting was done with antibodies directed against EphA2, HPTP, and phosphotyrosine.

Results

Expression and Purification of the LMW-PTP

LMW-PTPs can be purified using a two-step purification scheme involving cation-exchange chromatography (typically using a SP-Sephadex C-50 column) followed by size exclusion chromatography (typically using a Sephadex G50 column). A minor difference between the recombinant protein (isolated after expression in *E. coli*) and the native bovine or human protein is that the recombinant protein is not acetylated on the N-terminal alanine residue as in the native tissue protein. In this Example, WT-BPTP, D129A-BPTP, and C12A-BPTP were expressed and purified using the pET-11 expression system. A stock supply of the purified proteins, HPTP-A and HPTP-B, was already on hand.

Expression and purification of WT-BPTP from *E. coli* occurred without difficulty and generated good quantities of protein (40-50 mg per liter of expression medium). Expression of recombinant, mutant PTPases resulted in less protein (approximately 10-15 mg per liter of expression medium). In the case of the D129A bovine mutant, the induction period was increased to six hours, and the wash buffer was changed to 1 mM EDTA to increase the binding of the mutant proteins to the C50-columns. Once purified, the protein was stable for months at −20° C. in phosphate buffer.

Comparison of the LMW-PTP in MCF-10A (Neo) and MDA-MB-231 Cell Lines

Protein levels. EphA2 is tyrosine phosphorylated in the non-transformed MCF-10A (Neo) cell line, but not in the malignant MDA-MB-231 cell line.

Endogenous protein levels of the LMW-PTP in the MCF-10A (Neo) and the MDA-MB-231 cell lines were first compared by immunoblotting analyses. The results revealed lower protein levels of the LMW-PTP in the MCF-10A (Neo) cell line relative to the levels of the protein in the MDA-MB-231 cell line. This suggests that the higher protein levels of the LMW-PTP observed in the MDA-MB-231 cell line might correlate with EphA2 being substantially more dephosphorylated in that cell line compared to MCF-10A (Neo) cell line.

Although EphA2 is tyrosine phosphorylated in MCF-10A (Neo) cells, even higher levels of tyrosine phosphorylation of the cells can be achieved if EphA2 is treated with a soluble form of its ligand or artificially activated at the cell surface (Zantek, N. D. (1999), Ph.D. Thesis, Purdue University). With this in mind, it may also be suggested that the LMW-PTP dephosphorylates EphA2 in MCF-10A (Neo) cells, but not to the same degree as in the MDA-MB-231 cells. There might be a competition between phosphorylation and dephosphorylation of EphA2, and that in MDA-MB-231 cells the balance is tilted toward dephosphorylation. However, in the MCF-10A (Neo) cells, the balance is not tilted substantially in one direction or the other. As a result, EphA2 retains some of its tyrosine phosphorylation in the MCF-10A (Neo) cell line.

Subcellular localization. A panel of polyclonal and monoclonal antibodies, all directed against the LMW-PTP, was used to stain MCF-10A (Neo) and MDA-MB-231 cells. To determine the subcellular localization of the LMW-PTP in the MCF-10A (Neo) and MDA-MB-231, cells were grown on coverslips overnight. After fixation and permeabilization, the cells were stained with a primary antibody to detect the LMW-PTP. A fluorescent tag attached to the secondary antibody facilitated observation of the subcellular location of the LMW-PTP on the fluorescence microscope. The LMW-PTP was found to be diffuse and widely distributed in the MCF-10A (Neo) cells. When MDA-MB-231 cells were stained, the LMW-PTP was found localized in the membrane ruffles. This was an exciting finding because EphA2 was known to localize in the membrane ruffles in the MDA-MB-231 cell line, as well (Zantek, N. D. (1999), Ph.D. Thesis, Purdue University).

In Vitro Protein-Protein Interaction Between the LMW-PTP and EphA2

Co-immunoprecipitation, Attempts were made to co-immunoprecipitate the two proteins with separate antibodies directed against either protein. Co-immunoprecipitation of the LMW-PTP was readily detectable when immunoprecipitating with D7, an EphA2-specific antibody, followed by immunoblotting analyses with either the 7.1 or 10.0 LMW-PTP antibody. The co-immunoprecipitation was more evident when blotting with the 10.1 antibody. As would be predicted from the relative protein level analysis of the LMW-PTP, more LMW-PTP was co-immunoprecipitated from the MDA-MB-231 cell line than from the MCF-10A (Neo) cell line. A somewhat less dramatic result was obtained when immunoprecipitating with either the 7.1 or 10.1 antibody, followed by immunoblotting with the D7 antibody. Bands appeared in the lanes of the 7.1 and 10.1 IPs that were roughly co-linear with those of the D7 IP control. This suggests that these bands might represent EphA2.

It was somewhat surprising that co-immunoprecipitation of the proteins occurred in both of our cell lines. It was predicted that an interaction would be detected, but this was expected to be more likely in the MCF-10A (Neo) cell line because EphA2 is tyrosine phosphorylated there. However, because the interaction of a phosphatase with its substrate is either so transient or so weak, it was also thought that the interaction might not be easily detected. In our case, an interaction was detected in both cell lines.

In Vitro Dephosphorylation

Attempts at substrate trapping to detect direct interaction between EphA2 and LMW-PTP failed, so an alternative in vitro test was conducted. We examined the ability of pure LMW-PTP to dephosphorylate EphA2 isolated by immunoprecipitation. We found that the LMW-PTP dephosphorylated EphA2 in an enzyme concentration-dependent and a time-dependent manner.

As would be expected, the extent of dephosphorylation of EphA2 by the LMW-PTP was found to be greater when larger amounts of phosphatase are used than in cases when smaller amounts are used. The enzyme concentration-dependent dephosphorylation of EphA2 by the LMW-PTP is consistent with the hypothesis that high levels of LMW-PTP suppress tyrosine phosphorylation of EphA2 in MDA-MB-231 cells. It is thought that the higher LMW-PTP levels cause substantial dephosphorylation of EphA2 in those cells. The enzyme concentration-dependent dephosphorylation of EphA2 follows basic kinetic behavior. The rate of the reaction increases with increasing enzyme concentration. As a result, there is greater turnover per unit time. When the progress of the reaction is studied over longer periods of time, it is found that greater enzyme concentrations continue to dephosphorylate EphA2 in comparison with smaller enzyme concentrations. The leveling off of dephosphorylation that is observed may be due to instability of the protein under very dilute conditions.

In Vivo Protein-Protein Interaction Between the LMW-PTP and EphA2

Vector construction. To explore the effects of overexpressing the LMW-PTP in the MCF-10A (Neo) cell line, a pcDNA3 eukaryotic expression vector containing the coding region of the LMW-PTP was constructed. Microgram amounts of the pET-11d plasmid were isolated without difficulty using a commercially available DNA purification kit. Primers were designed and used to amplify the coding region of the A- and B-isoforms of the LMW-PTP.

The PCR products were purified using a commercially available PCR product purification kit from QIAGEN. The amplified coding regions of the LMW-PTP isoenzymes were digested with BamH I and Hind III to remove the extensions. The "sticky-ends" that were produced allowed for directional cloning of the inserts in the mammalian expression vector, pcDNA3, which was also digested with Hind III and BamH I. Digestion of the isoenzymes generated 491 bp fragment. Digestion of the pcDNA3 vector generated an open vector with 18 fewer base pairs than the circular vector.

After cell transformation, the constructed vectors were isolated from the cells and screened with a panel of restriction enzymes to determine if the coding regions of the human A- and B-isoenzymes of LMW-PTP were present. The coding regions were present in their respective vectors as indicated by the cuts produced by the restriction enzymes.

Overexpression of the LMW-PTP in MCF-10A (Neo) cells. Overexpression of the LMW-PTP in the MCF-10A (Neo) cell line was attempted in order to explore the effects of increased protein levels of the phosphatase on EphA2's tyrosine phosphorylation status. Large quantities of the constructed vectors were isolated in a highly pure form using a commercially available DNA purification kit. Isolation of the vectors using this procedure occurred without great difficulty. The commercially available transfection kit, FuGENE, was used to transfect the MCF-10A (Neo) cell line with "empty" pcDNA3, HPTP-A/pcDNA3 and HPTP-B/pcDNA3, respectively. The "empty" vector served as a control in the experiments such that any changes in EphA2's tyrosine phosphorylation status should be attributable to increased levels of the LMW-PTP and not to the presence of the mammalian expression vector.

Overexpression of the HPTP-B in the MCF-10A (Neo) cell line resulted in decreased tyrosine phosphorylation levels of EphA2. No noticeable difference in EphA2's tyrosine phosphorylation was seen when HPTP-A was overexpressed in the same cell line. From this information, it might be concluded that the interaction of EphA2 the LMW-PTP is isoenzyme specific, which is not an unreasonable possibility. Differences in the amino acid sequence of the isoenzymes could be the underlying reason why only one isoenzyme appears to interact preferentially with EphA2. However, there are many other reasons that explain the difference as well.

Discussion

In transformed breast epithelia such as MDA-MB-231, EphA2 is not tyrosine phosphorylated. However, restoration of tyrosine phosphorylation of EphA2 occurs when these cells are treated with the pervanadate ion (Zantek, N. D. (1999), Ph.D. Thesis, Purdue University). This gives a strong indication that a PTPase is causing the loss of tyrosine phosphorylation of EphA2. Also, treatment of EphA2 with a soluble form of the ephrinA1 ligand and cross-linking of EphA2 at the surface of the cell leads to transient tyrosine phosphorylation of EphA2. The loss of tyrosine phosphorylation of EphA2 that occurs over time with these treatments could be due to a PTPase interacting with EphA2.

Example II

Regulation of EphA2 by Low Molecular Weight Protein Tyrosine Phosphatase

Materials and Methods

Cell Lines and Antibodies. Human breast (MCF-10A, MCF 10A ST, MCF-7, MDA-MB-231, MDA-MB435, SK-BR-3) epithelial cells were cultured as described in Example I and previously (Paine, T. M., Soule, H. D., Pauley, R. J. & Dawson, P. J. (1992) *Int J Cancer* 50, 463-473; Jacob, A. N., Kalapurakal, J., Davidson, W. R., Kandpal, G., Dunson, N., Prashar, Y. & Kandpal, R. P. (1999) *Cancer Detection & Prevention* 23, 325-332; Shevrin, D. H., Gorny, K. I. & Kukreja, S. C. (1989) *Prostate* 15, 187-194). Monoclonal antibodies specific for phospho-tyrosine (PY20) and β-catenin were purchased from Transduction Laboratories (Lexington, Ky.). Monoclonal antibodies specific for phosphotyrosine (4G10) and EphA2 (clone D7) were purchased from Upstate Biotechnology, Inc. (Lake Placid, N.Y.). Monoclonal antibodies against vinculin were purchased from NeoMarkers (Fremont, Calif.).

Cell Lysates. Cell lysates were harvested and normalized for equal loading as described previously (Kinch, M. S., Clark, G. J., Der, C. J. & Burridge, K. (1995) *J Cell Biol* 130,461-471). To confirm equal loading, blots were stripped as described previously and reprobed with antibodies specific to β-catenin or vinculin (Kinch, M. S., Clark, G. J., Der, C. J. & Burridge, K. (1995) *J Cell Biol* 130, 461-471).

Immunoprecipitation and Western Blot Analyses: Immunoprecipitation of EphA2 or LMW-PTP were performed using rabbit anti-mouse (Chemicon, Temecula, Calif.) conjugated Protein A Sepharose (Sigma, St. Louis, Mo.) as described previously (Zantek, N. D., Azimi, M., Fedor-Chaiken, M., Wang, B., Brackenbury, R. & Kinch, M. S. (1999) *Cell Growth & Differentiation* 10, 629-638). To confirm equal loading, blots were stripped as described previously (Kinch, M. S., Clark, G. J., Der, C. J. & Burridge, K. (1995) *J Cell Biol* 130, 461471) and reprobed with EphA2 or LMW-PTP specific antibodies. Western blot analysis were performed on normalized cells lysates and immunoprecipitations as detailed (Zantek, N. D., Azimi, M., Fedor-Chaiken, M., Wang, B., Brackenbury, R. & Kinch, M. S. (1999) *Cell Growth & Differentiation* 10, 629-638). Antibody binding was detected by enhanced chemiluminescence, (ECL; Pierce, Rockford, Ill.), and visualized by autoradiography (Kodak X-OMAT; Kodak, Rochester, N.Y.).

EGTA and Pervanadate Treatments. "Calcium Switch" experiments were performed as described previously (Zantek, N. D., Azimi, M., Fedor-Chaiken, M., Wang, B., Brackenbury, R. & Kinch, M. S. (1999) *Cell Growth & Differentiation* 10, 629-638) using MCF-10A cells grown to 70% confluence and medium containing a final concentration of 4 mM EGTA. Pervanadate was added to MDA-MB-231 in monolayer culture at a final concentration of 0, 1, 10 or 100 mM and the treatment was allowed to incubate for 10 minutes at 37° C., 5% $CO_2$. For the combined EGTA-Pervanadate Treatment, MDA-MB-231 cells were first treated with 100 mM Pervanadate and were then subjected to the EGTA treatment.

In Vitro Kinase and Phosphatase Assays. To evaluate LMW-PTP activity against EphA2, EphA2 was immunoprecipitated from MCF-10A cells and incubated with purified LMW-PTP protein at a concentration of 0.45, 7.8, or 26.5 mg/mL for 0, 5, 15, or 30 minutes. The assay was terminated through the addition of Laemmli sample buffer. The phosphotyrosine content of the EphA2 in the treatments was then observed using Western blot analysis with antibodies specific to phosphotyrosine. To determine in vitro autophosphorylation activity, immunoprecipitated EphA2 was evaluated using in vitro kinase assays as detailed previously (Zantek, N. D., Azimi, M., Fedor-Chaiken, M., Wang, B., Brackenbury, R. & Kinch, M. S. (1999) Cell Growth & Differentiation 10, 629-638).

Transfection and Selection. Monolayers of MCF-10A cells were grown to 30-50% confluence and were transfected with pcDNA3.1-LMW-PTP or pcDNA3.1-D 129A-LMW-PTP using Lipofectamine PLUS (Life Technologies, Inc., Grand Island, N.Y.). As a control for the transfection procedure, empty pcDNA3.1 vector was transfected into the same cell line in parallel. Transient transfections were allowed to grow for 48 hours post-transfection. For stable lines, neomycin-resistant cells were selected in growth medium containing 16 mg/mL neomycin (Mediatech, Inc., Herndon, Va.). To confirm LMW-PTP overexpression, Western blot analysis was performed using LMW-PTP specific antibodies. Parental cells and cells transfected with empty pcDNA3.1 vector were used as negative controls.

Growth Assay. To evaluate cell growth using monolayer assays, $1 \times 10^5$ cells were seeded into tissue-culture treated multi-well dishes for 1, 2, 4 or 6 days in triplicate experiments. Cell numbers were evaluated by trypsin suspension of the samples followed by microscopic evaluation using a hemacytometer. Soft agar colony formation was performed and quantified as detailed (Zelinski, D. P., Zantek, N. D., Stewart, J., Irizarry, A. & Kinch, M. S. (2001) Cancer Res 61, 2301-2306); Clark, G. J., Kinch, M. S., Gilmer, T. M., Burridge, K. & Der, C. J. (1996) Oncogene 12, 169-176). For experiments with EphA2 antisense, cells were incubated with oligonucleotides prior to suspension in soft agar. The data shown is representative of at least three different experiments.

Antisense Treatment. Monolayers of MCF-10A Neo cells and MCF-10A cells stably overexpressing LMW-PTP were grown to 30% confluence and were transfected with EphA2 antisense oligonucleotides as detailed. Samples that had been transfected with an inverted EphA2 antisense oligonucleotide or with the transfection reagent alone provided negative controls.

Results

Figure 2:
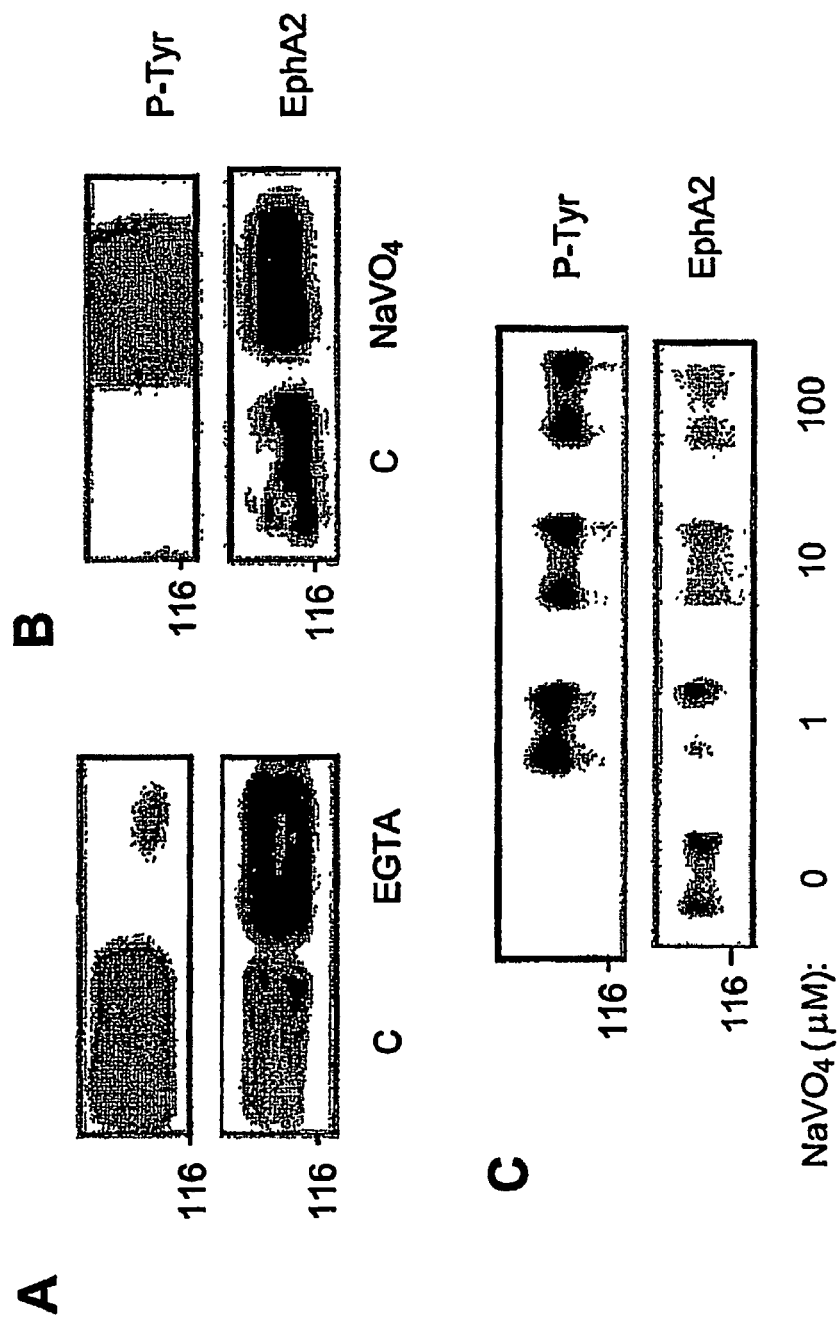
FIG. 2 shows that EphA2 is regulated by an associated phosphatase. (A) Monolayers of MCF-10A human mammary epithelial cells were incubated in the presence or absence (denoted as "C" for control) of 4 mM EGTA for 20 minutes before detergent extraction. The samples were resolved by SDS-PAGE and probed with phosphotyrosine-specific antibodies (PY20 and 4G10; top). The membranes were stripped and reprobed with EphA2 specific antibodies to confirm equal sample loading (below). (B) MCF-10A cells were treated with EGTA, as detailed above, in the presence of absence of $NaVO_4$ to inhibit phosphatase activity. (B) EphA2 was immunoprecipitated from MDA-MB-231 cells that had been incubated in the presence of the indicated concentrations of $NaVO_4$ for 10 minutes at 37° C.

EphA2 is Regulated by an Associated Tyrosine Phosphatase Several independent lines of investigation suggested that EphA2 is regulated by an associated tyrosine phosphatase. First, EphA2 could be rapidly dephosphorylated in non-transformed epithelial cells. Western blot analysis with phosphotyrosine antibodies (PY20 or 4G10) indicated lower levels of EphA2 phosphotyrosine content within 5 minutes following EGTA-mediated disruption of EphA2-ligand binding (FIG. 2A). Similarly, tyrosine phosphorylation of EphA2 decreased following incubation of non-transformed epithelial cells with dominant-negative inhibitors of EphA2-ligand binding (e.g., EphA2-Fc). Identical results were obtained using multiple non-transformed epithelial cell systems, including MCF-12A, MCF10-2, HEK293, MDCK and MDBK cells. Based on these findings, we asked whether tyrosine phosphatase inhibitors could prevent the loss of EphA2 phosphotyrosine content in response to EGTA treatment. Indeed, inhibitors such as sodium orthovanadate prevented the decrease in EphA2 phosphotyrosine following treatment of MCF-10A cells with EGTA (FIG. 2B).

Previous studies by our laboratory have shown that the phosphotyrosine content of EphA2 is greatly reduced in malignant epithelial cells as compared with non-transformed epithelia (Zelinski, D. P., Zantek, N. D., Stewart, J., Irizarry, A. & Kinch, M. S. (2001) Cancer Res 61, 2301-2306; Zantek, N. D., Azimi, M., Fedor-Chaiken, M., Wang, B., Brackenbury, R. & Kinch, M. S. (1999) Cell Growth & Differentiation 10, 629-638). Thus, we asked if tyrosine phosphatase activity could contribute to the reduced phosphotyrosine content of EphA2 in malignant cells. Whereas EphA2 was not tyrosine phosphorylated in malignant breast cancer cells (MDA-MB-231, MDA-435, MCFneoST, or PC-3 cells), incubation with increasing concentrations of sodium orthovanadate induced rapid and vigorous tyrosine phosphorylation of EphA2 (FIG. 2C). As vanadate treatment of cells can often lead to exaggerated phosphorylation of physiologically irrelevant sites, we performed phosphopeptide-mapping studies using EphA2 that had been labeled with 32P-ATP either in vitro or in vivo. These studies revealed identical patterns of tyrosine phosphorylation in non-transformed MCF-10A cells and vanadate treated MDA-MB-231 cells. Although the cytoplasmic domain contains multiple sites that could have been phosphorylated promiscuously, these were not phosphorylated under the conditions utilized here, suggesting that vanadate had not increased the phosphorylation of irrelevant sites. Altogether, these results indicate that EphA2 is regulated by an associated phosphatase that suppresses EphA2 phosphotyrosine content in malignant cells.

LMW-PTP Interacts with and Dephosphorylates EphA2

Figure 3:
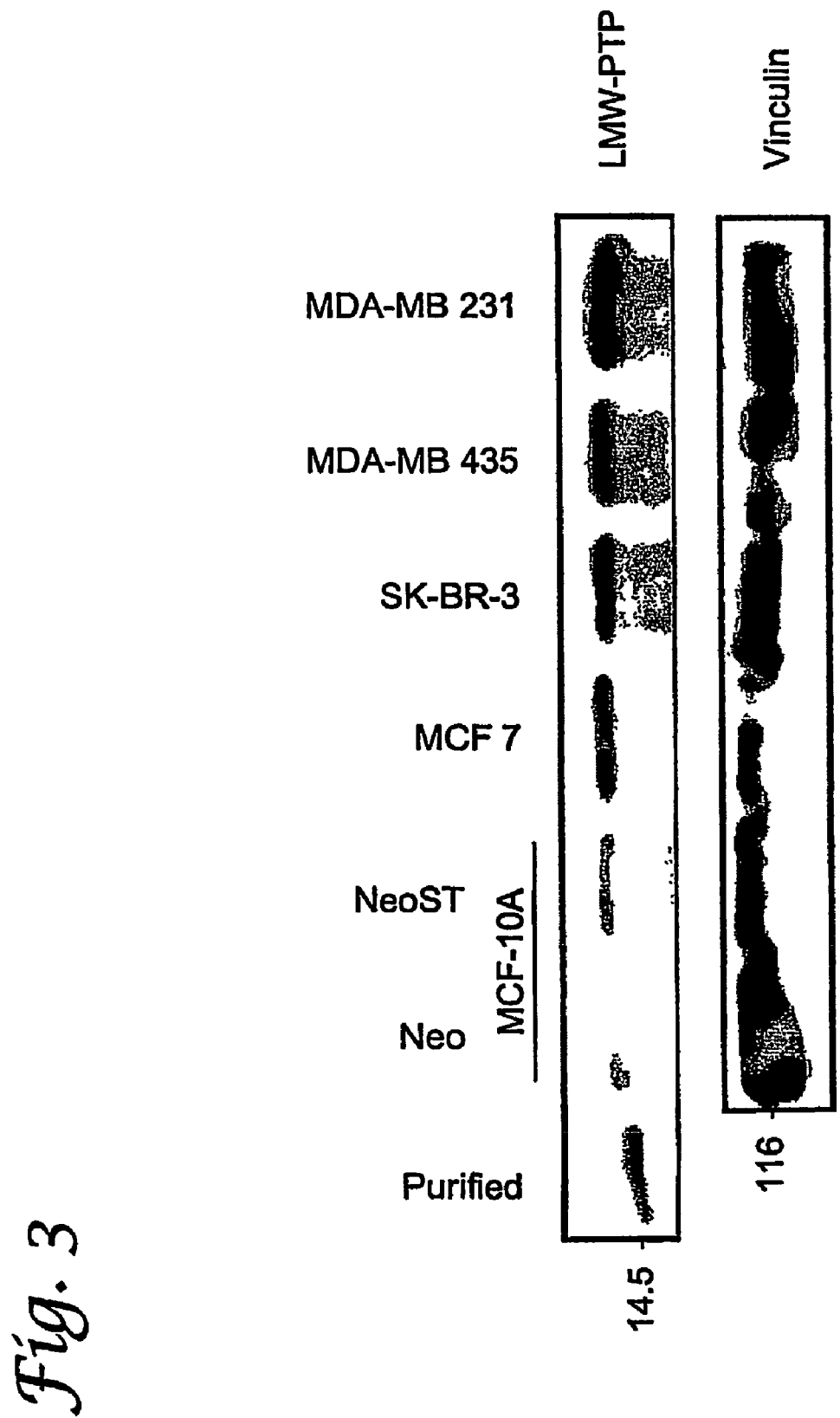
FIG. 3 shows that LMW-PTP protein levels are elevated in malignant cell lines. Detergent lysates (lanes 2-7) were harvested from non-transformed (MCF-10Aneo), oncogene transformed (MCF-10AneoST), and tumor derived (MCF-7, SK-BR-3, MDA-MB-435, MDA-MB-231) mammary epithelial cells. The samples were resolved by SDS-PAGE and subjected to Western Blot analysis using LMW-PTP specific antibodies (top). Purified LMW-PTP (lane 1) provided a positive control for western blot analyses. The membranes were then stripped and reprobed with antibodies specific to vinculin to evaluate sample loading (bottom). Note that LMW-PTP is overexpressed in tumor-derived cells despite the relative over-loading of the non-transformed (MCF-10Aneo) samples.

To identify tyrosine phosphatases that might regulate EphA2 in malignant cells, we considered a recent report that LMW-PTP regulates a related molecule, EphB4 (Jacob, A. N., Kalapurakal, J., Davidson, W. R., Kandpal, G., Dunson, N., Prashar, Y., and Kandpal, R. P. (1999) Cancer Detect. Prev. 23, 325-33). Our initial experiments began to catalog the expression and function of LMW-PTP in non-transformed (MCF-10A Neo) and malignant (MCF-7, SK-BR-3, MDA-MB435, MDA-MB-231) mammary epithelial cells (FIG. 3). Western blot analyses of whole cell lysates revealed relatively high levels of LMW-PTP in tumor-derived breast cancer cells as compared with non-transformed MCF-10A mammary epithelial cells. To confirm equal sample loading, the membranes were stripped and re-probed with antibodies against a control protein (Vinculin), verifying that the high levels of LMW-PTP did not reflect a loading error or a generalized increase in protein levels in the malignant cells. A malignant variant of MCF-10A, MCFneoST, also demonstrated elevated LMW-PTP expression, which was intriguing based on a recent report that EphA2 is not tyrosine phosphorylated in those cells (Zantek, N. D., Walker-Daniels, J., Stewart, J. C., Hansen, R. K., Robinson, D., Miao, H., Wang, B., Kung, H. J., Bissell, M. J. & Kinch, M. S. (2001) Clin Cancer Res 7, 3640-3648). The use of a genetically-matched system also precluded potential differences due to cell origin or culture conditions. Thus, the highest levels of LMW-PTP were consistently found in malignant epithelial cells and inversely related to EphA2 phosphotyrosine content.

Figure 4:
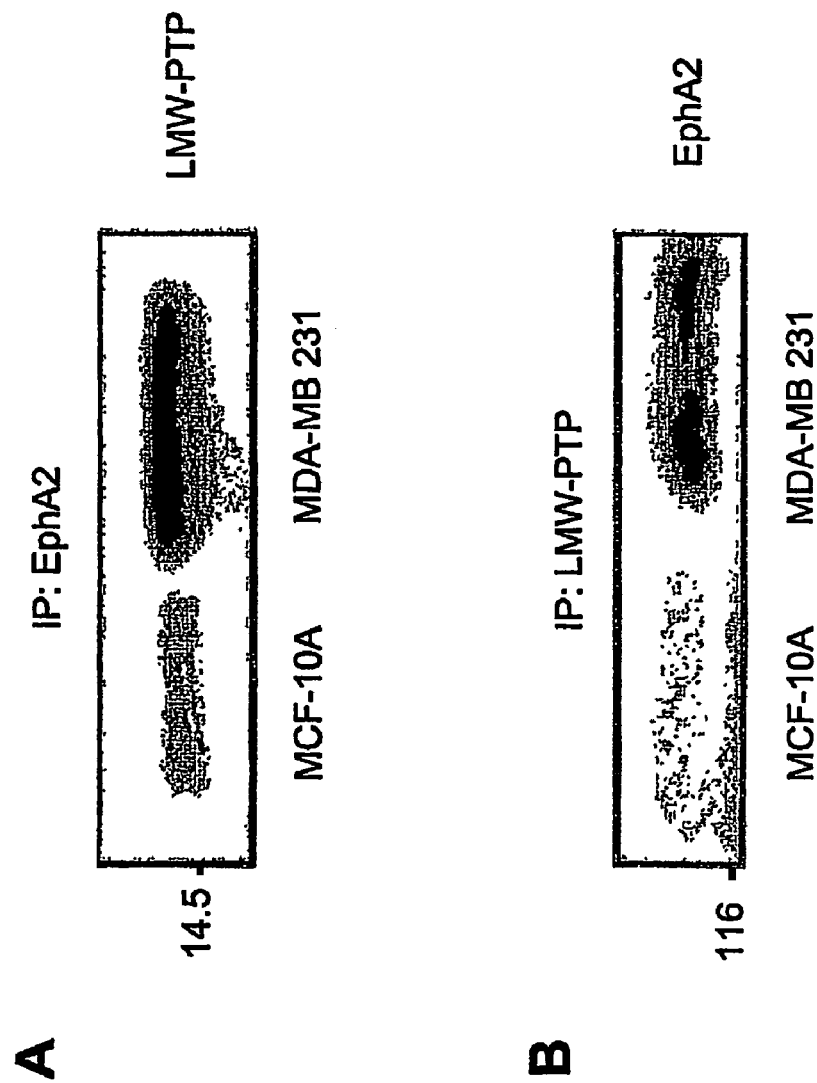
FIG. 4 shows that EphA2 and LMW-PTP form a molecular complex in vivo. (A) Complexes of EphA2 were immunoprecipitated from $5 \times 10^6$ MCF-10A or MDA-MB-231 cells, resolved by SDS-PAGE and subjected to Western blot analyses with antibodies specific for LMW-PTP. (B) To confirm complex formation, complexes of LMW-PTP were similarly isolated by immunoprecipitation and probed with EphA2 specific antibodies.

The results above provided suggestive, but indirect, evidence that LMW-PTP might negatively regulate the phosphotyrosine content of EphA2 in tumor cells. To explore this hypothesis further, we first asked if the two molecules interacted in vivo. EphA2 was immunoprecipitated from MDA-MB-231 cells using specific antibodies (clone D7) and these complexes were resolved by SDS-PAGE. Subsequent Western blot analyses revealed that LMW-PTP was prominently found within EphA2 immune complexes (FIG. 4A). The inverse experiment confirmed that EphA2 could similarly be detected in complexes of immunoprecipitated LMW-PTP (FIG. 4B). Control immunoprecipitations with irrelevant antibodies confirmed the specificity of the interactions of the two molecules.

Figure 5:
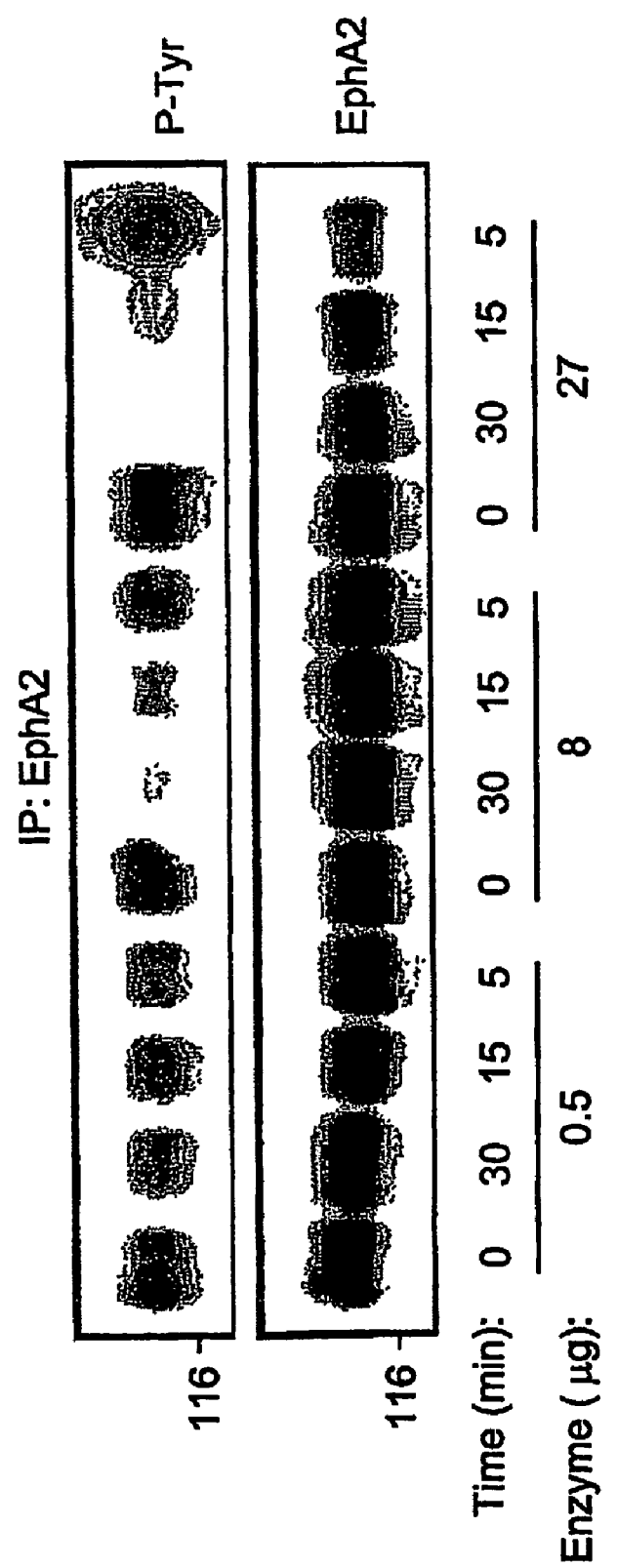
FIG. 5 shows that EphA2 can serve as a substrate for LMW-PTP in vitro. EphA2 was immunoprecipitated from $5 \times 10^6$ MCF-10A cells before incubation with the indicated amounts of LMW-PTP protein for 0-30 minutes at 37° C. The samples were then resolved by SDS-PAGE and subjected to Western blot analysis with phosphotyrosine-specific antibodies. The membranes were stripped and reprobed with EphA2 specific antibodies to confirm equal sample loading.

The co-immunoprecipitation studies did not clarify whether EphA2 can serve as a substrate for LMW-PTP. To address this directly, EphA2 was immunoprecipitated from MCF-10A cells, where it is normally tyrosine phosphorylated. The purified EphA2 was then incubated with different concentrations of purified LMW-PTP before Western blot analyses of EphA2 with phosphotyrosine-specific antibodies (PY20 and 4G10). These experiments demonstrated that purified LMW-PTP could dephosphorylate EphA2 in a dose and time-dependent manner (FIG. 5A).

Figure 6:
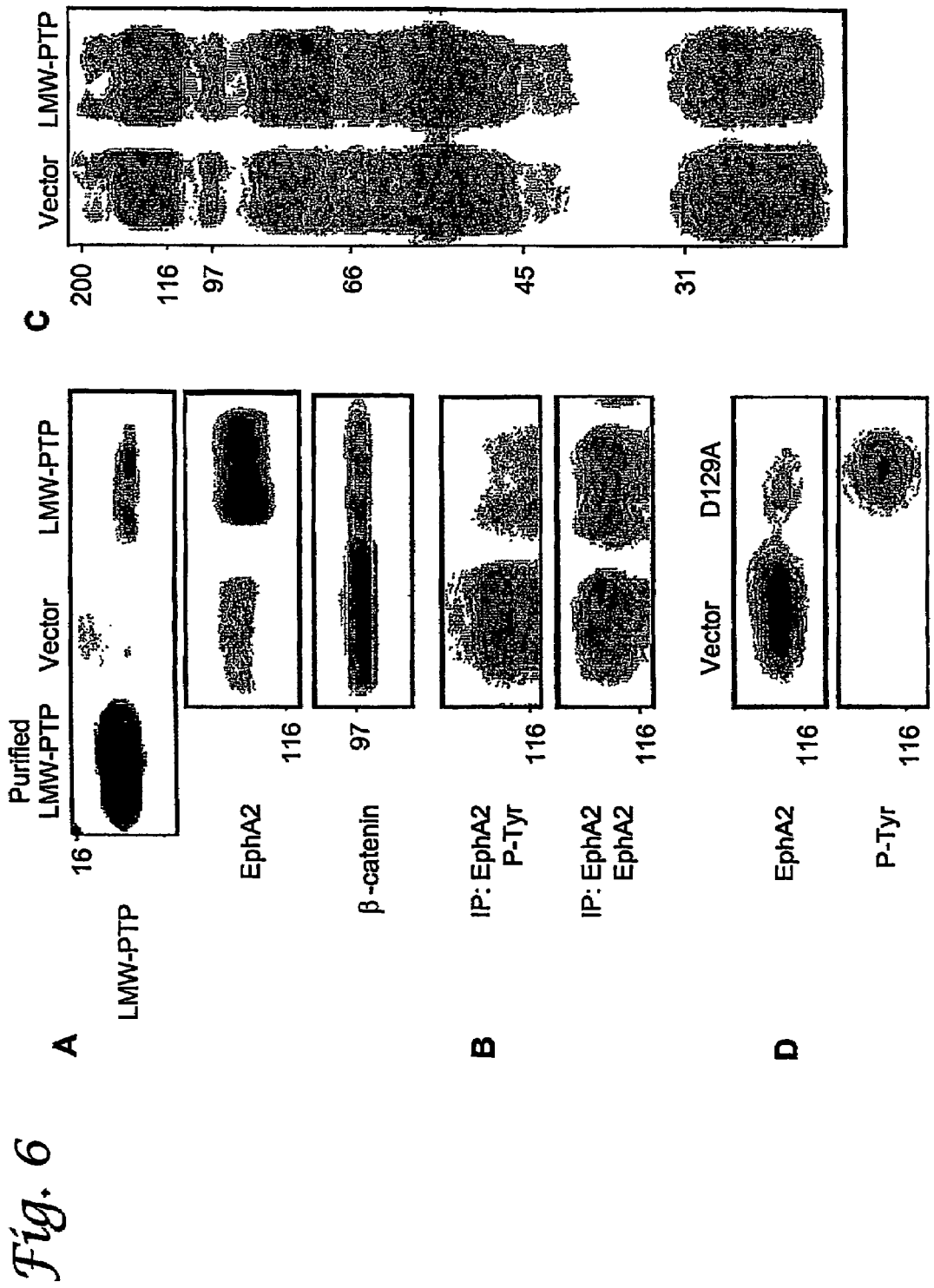
FIG. 6 shows that LMW-PTP dephosphorylates EphA2 in vivo. (A) MCF-10A cells were stably transfected with expression vectors that encode for wild-type LMW-PTP. Detergent lysates were resolved by SDS-PAGE and subjected to Western blot analyses with LMW-PTP antibodies to confirm LMW-PTP overexpression, with purified LMW-PTP providing a positive control. Parallel samples were then probed with antibodies specific for α-catenin as a loading control. (B) EphA2 was immunoprecipitated and Western blot were performed using EphA2 (top) and P-Tyr (bottom)-specific antibodies. (C) The overall levels of phosphotyrosine in control and LMW-PTP-transfected cells were compared using specific antibodies. Note that equal amounts of EphA2 were utilized for these results to overcome differences in endogenous EphA2 expression (in contrast to part B). (D) The protein levels (top) and phosphotyrosine content of EphA2 in MDA-MB-231 cells that had been transfected with a dominant negative form of LMW-PTP (D129A) or a matched vector control were evaluated by Western blot analyses. Note the consistent findings that LMW-PTP activity relates to decreased EphA2 phosphotyrosine content and increased EphA2 protein levels.

Although in vitro studies indicated that EphA2 could be phosphorylated by LMW-PTP in vitro, we recognized that in vitro studies are not always be representative of the analogous situation in vivo. Thus, LMW-PTP was ectopically overexpressed in MCF-10A cells. This particular cell system was selected because non-transformed MCF-10A cells have low levels of endogenous LMW-PTP and because the EphA2 in these non-transformed epithelial cells is normally tyrosine phosphorylated. Ectopic overexpression of LMW-PTP was achieved by stable transfection, as determined by Western blot analyses with specific antibodies (FIG. 6A). Importantly, overexpression of LMW-PTP was sufficient to reduce the phosphotyrosine content of EphA2 as compared with vector-transfected negative controls (FIG. 6A). Identical results were obtained using different experiments, with different transfectants and in both stably and transiently-transfected samples, thus eliminating potential concerns about clonal variation. Moreover, the decreased phosphotyrosine content was specific for EphA2 as the phosphotyrosine content LMW-PTP overexpressing cells was not generally decreased (FIG. 6B).

LMW-PTP Overexpression Causes Malignant Transformation of Epithelial Cells

Figure 7:
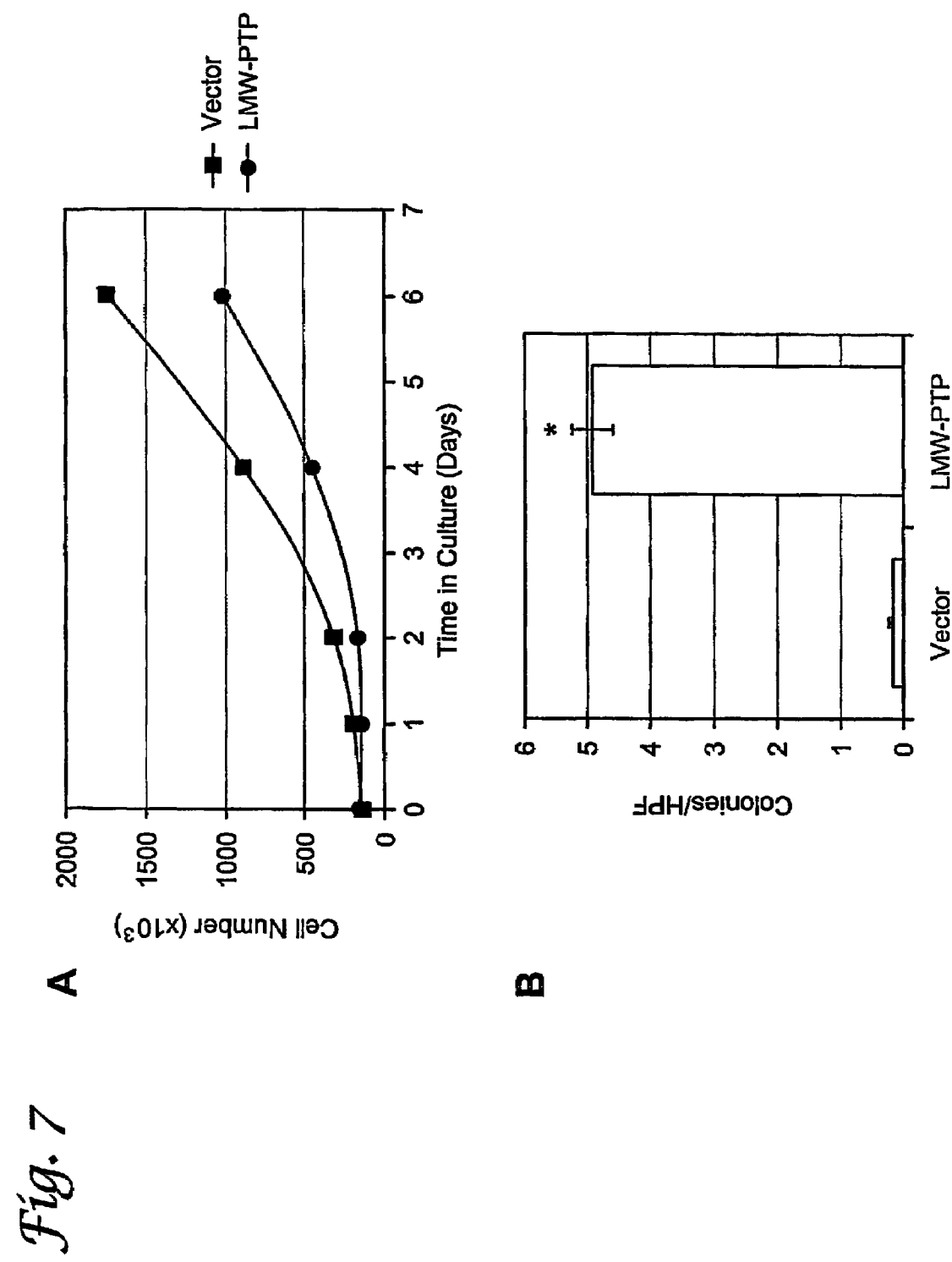
FIG. 7 shows that LMW-PTP enhances malignant character. (A) To evaluate anchorage-dependent cells growth, $1 \times 10^5$ control or LMW-PTP transfected MCF-10A cells were seeded into monolayer culture and cell numbers were evaluated microscopically at the intervals shown. (B) In parallel studies, the control and LMW-PTP transfected cells were suspended in soft agar. Shown is colony formation (per high powered field) after five days of incubation at 37° C. These results were representative of at least three separate experiments. * Indicates $p<0.01$.

Tyrosine phosphorylated EphA2 negatively regulates tumor cell growth whereas unphosphorylated EphA2 acts as a powerful oncoprotein (Zelinski, D. P., Zantek, N. D., Stewart, J., Irizarry, A. & Kinch, M. S. (2001) Cancer Res 61, 2301-2306; Zantek, N. D., Azimi, M., Fedor-Chaiken, M., Wang, B., Brackenbury, R. & Kinch, M. S. (1999) Cell Growth & Differentiation 10, 629-638). Thus, we asked whether overexpression of LMW-PTP would be sufficient to induce malignant transformation. To address this question, we utilized the MCF-10A cells, described above, which had been transfected with either wild-type LMW-PTP or a vector control. Our initial studies evaluated the growth rates of control and LMW-PTP-overexpressing cells in monolayer culture. When evaluated using standard, two-dimensional culture conditions, the growth rates of LMW-PTP-overexpressing MCF-10A cells were significantly lower than the growth rates of matched controls (P<0.05) (FIG. 7A).

Two-dimensional assessments of growth often do not reflect the malignant character of tumor cells. Instead, three-dimensional analyses of cell behavior using soft agar and reconstituted basement membranes can provide a more relevant way of assessing malignant behavior. Whereas vector-transfected MCF-10A cells were largely incapable of colonizing soft agar, LMW-PTP-overexpressing cells formed an average of 4.9 colonies per high-powered microscope field (P<0.01; FIG. 7B). Based on recent findings with other three-dimensional assay systems, we also evaluated cell behavior using three-dimensional, reconstituted basement membranes. Consistent with a more aggressive phenotype, microscopic assessment of cell behavior in Matrigel confirmed the malignant character of LMW-PTP overexpressing cells. When plated atop or within Matrigel, LMW-PTP-overexpressing cells formed larger colonies than vector-transfected cells. Altogether, consistent results with multiple and different systems suggest that overexpression of LMW-PTP is sufficient to induce malignant transformation.

The Oncogenic Phenotype of LMW-PTP-Overexpressing Cells is Related to EphA2 Expression Tyrosine phosphorylation of EphA2 induces its internalization and degradation. Thus, we postulated that overexpression of LMW-PTP might increase the protein levels of EphA2. Indeed, Western blot analyses of whole cell lysates revealed higher levels of EphA2 in MCF-10A cells that overexpress LMW-PTP as compared with vector-transfected controls (FIG. 6A). Moreover, this EphA2 was not tyrosine phosphorylated (FIG. 6B). However, Western blot analyses revealed that the reduced phosphotyrosine content was selective for EphA2, as the general levels of phosphotyrosine were not altered in LMW-PTP transformed cells (FIG. 6C).

The finding that overexpression of LMW-PTP increased EphA2 expression and decreased its phosphotyrosine content was intriguing since this phenotype was reminiscent of highly aggressive tumor cells (Zelinski, D. P., Zantek, N. D., Stewart, J., Irizarry, A. & Kinch, M. S. (2001) Cancer Res 61, 2301-2306; Zantek, N. D., Azimi, M., Fedor-Chaiken, M., Wang, B., Brackenbury, R. & Kinch, M. S. (1999) Cell Growth & Differentiation 10, 629-638)). Thus, we asked whether selective targeting of LMW-PTP in malignant cells would impact EphA2. To accomplish this, an enzymatic mutant of LMW-PTP (D129A) that is catalytically inactive (Zhang, Z., Harms, E. & Van Etten, R. L. (1994) Journal of Biological Chemistry 269, 25947-25950) was overexpressed in MDA-MB-231 cells, which have high levels of wild-type LMW-PTP (FIG. 3) and overexpress unphosphorylated EphA2. Ectopic overexpression of LMW-PTPD129A was found to decrease the levels of EphA2. Moreover, Western blot analyses of immunoprecipitated material revealed that this EphA2 was tyrosine phosphorylated (FIG. 6C). Thus, consistent results indicate that overexpression of wild type LMW-PTP is necessary and sufficient to confer the overexpression and functional alterations of EphA2 that have been observed in tumor-derived cells.

Figure 8:
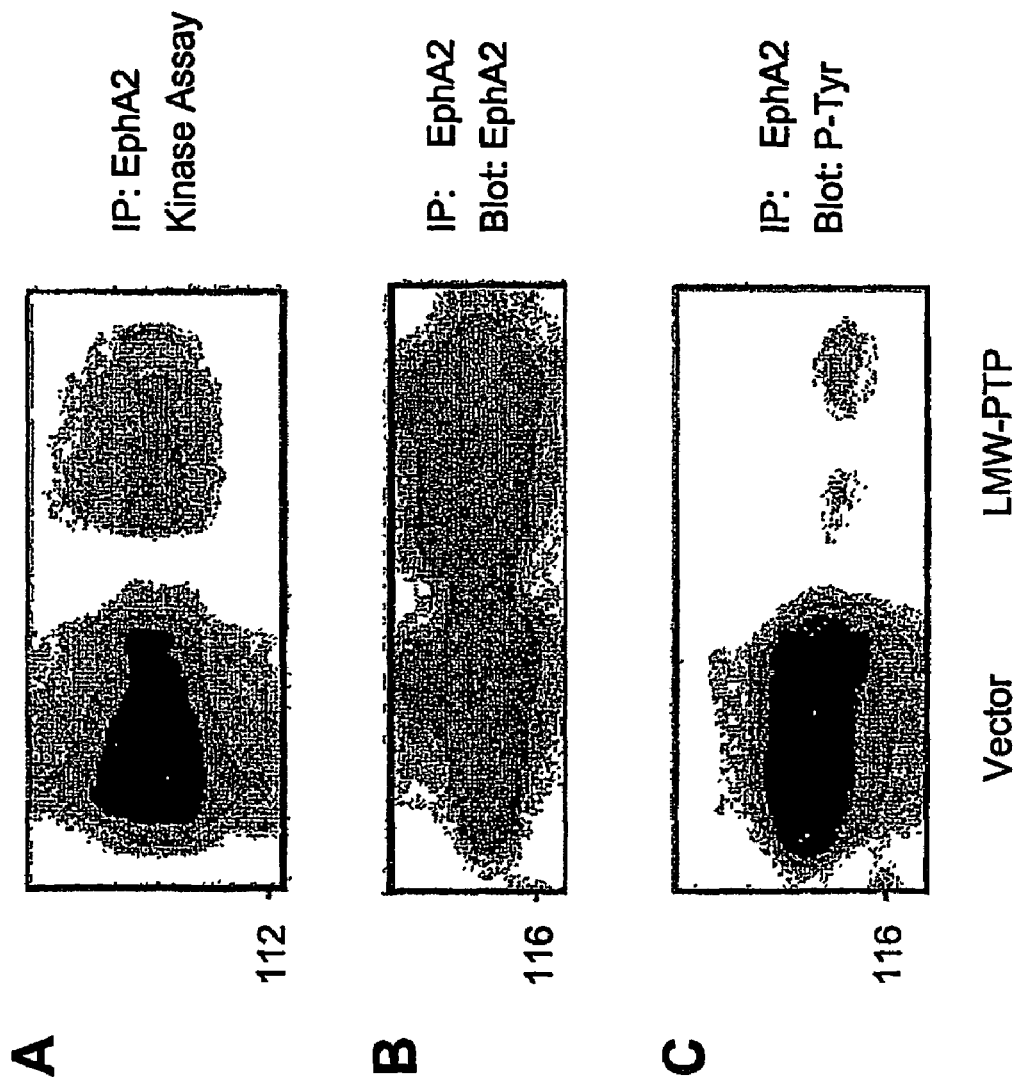
FIG. 8 shows that EphA2 retains enzymatic activity in LMW-PTP transformed cells. Equal amounts of EphA2 were immunoprecipitated from control or LMW-PTP transformed MCF-10A cells and subjected to in vitro kinase assays. (A) Autophosphorylation with $\gamma$-$^{32}$P-labeled ATP was evaluated by autoradiography. To confirm equal sample loading, a portion of the immunoprecipitated materials was evaluated by Western blot analyses with (B) EphA2 or (C) phosphotyrosine antibodies. Whereas EphA2 is not tyrosine phosphorylated in LMW-PTP transformed cells, it retains enzymatic activity. Note that equal amounts of EphA2 were utilized for these results to overcome differences in endogenous EphA2 expression (for example, See FIG. 5B).

Although the EphA2 in the LMW-PTP overexpressing MCF-10A cells was not tyrosine phosphorylated, it retained enzymatic activity. In vitro kinase assays verified that the EphA2 from LMW-PTP-transformed MCF-10A cells had levels of enzymatic activity that were comparable to vector-transfected controls (FIG. 8A). To verify equal sample loading, two controls were performed. Equal amounts of input lysate were verified by Western blot analyses with β-catenin antibodies. In addition, the immunoprecipitated EphA2 was divided and half of the material was resolved by SDS-PAGE and analyzed by Western blot analyses with EphA2 and phosphotyrosine-specific antibodies (FIG. 8B). Thus phosphorylated and unphosphorylated EphA2 were both capable of enzymatic activity.

Figure 9:
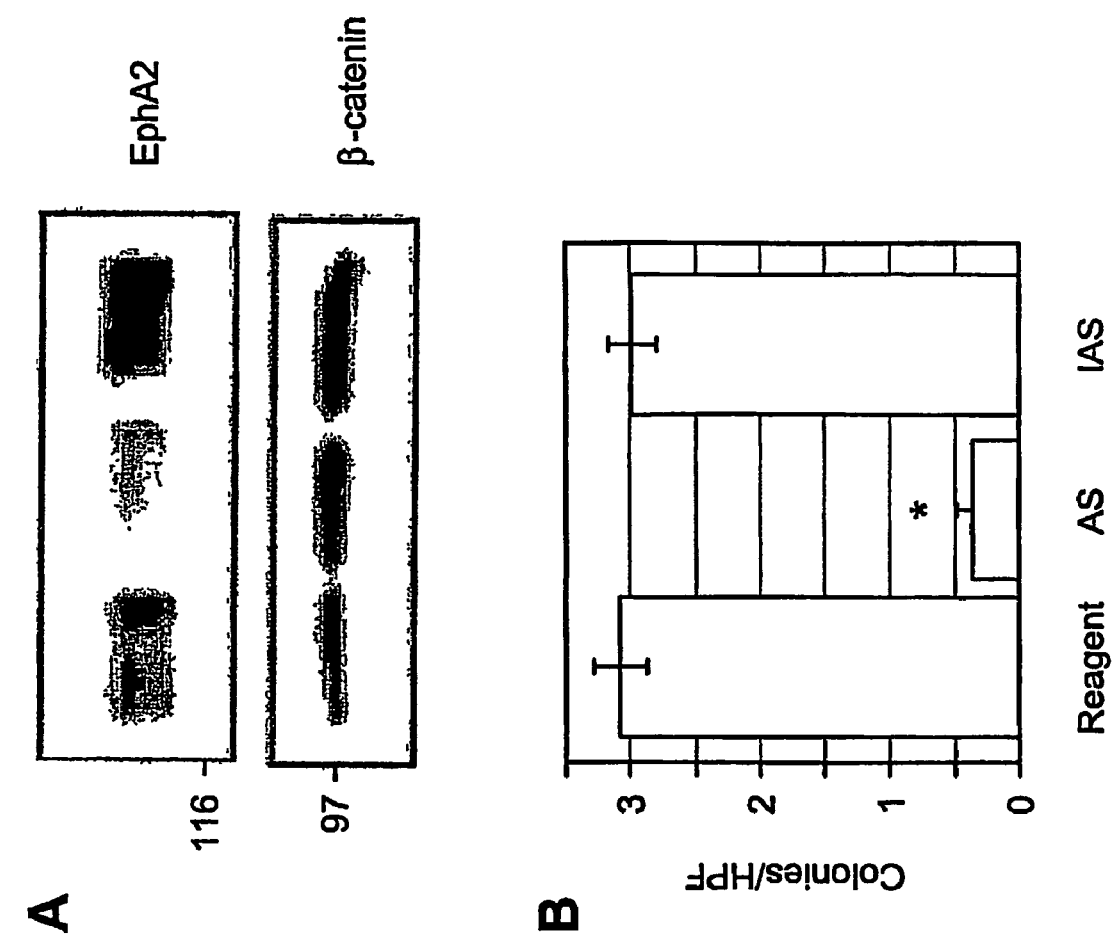
FIG. 9 shows that malignant transformation by LMW-PTP is related to EphA2 overexpression. MCF-10A cells were treated with EphA2 antisense (AS oligonucleotides, with inverted antisense (IAS) oligonucleotides or transfection reagents alone providing negative controls. (A) Western blot analysis using EphA2 specific antibodies confirmed that the antisense treatment decreased EphA2 protein levels (top). The membrane was then stripped and reprobed for β-catenin to confirm equal sample loading (bottom). (B) Parallel samples were suspended and incubated in soft agar for 5 days. Shown are the average number colonies per high-powered microscopic field (HPF). * Indicates $p<0.01$.

Since the levels of EphA2 were elevated in LMW-PTP transformed cells, we asked whether the oncogenic activity of EphA2 might have contributed to this phenotype. To address this, we utilized our experience with antisense strategies to selectively decrease EphA2 expression in LMW-PTP transformed cells (Hess A. R., Seftor, E. A., Gardner, L. M., Carles-Kinch, K., Schneider, G. B., Seftor, R. E., Kinch, M. S. & Hendrix, M. J. C. (2001) *Cancer Res* 61, 3250-3255). We verified the success of these strategies by Western blot analyses (FIG. 9A) and then asked if decreased EphA2 expression would alter soft agar colonization. Indeed, transfection with EphA2 antisense oligonucleotides decreased the soft agar colonization of LMW-PTP-transformed MCF-10A cells by at least 87% ($P<0.01$; FIG. 9B). In contrast, transfection of these cells with an inverted antisense control nucleotide control did not significantly alter soft agar colonization. Thus, we were able to exclude that the results with the antisense oligonucleotides had resulted from non-specific toxicities caused by the transfection procedure. Altogether, our results indicate that, in cells that express EphA2, the oncogenic actions of overexpressed LMW-PTP require high levels of EphA2.

Discussion

The major finding of our present study is that EphA2 is regulated by an associated tyrosine phosphatase and we identify LMW-PTP as a critical regulator of EphA2 tyrosine phosphorylation. We also demonstrate that LMW-PTP is overexpressed in metastatic cancer cells and that LMW-PTP overexpression is sufficient to confer malignant transformation upon non-transformed epithelial cell models. Finally, we demonstrate that LMW-PTP upregulates the expression of EphA2 and that the oncogenic activities of LMW-PTP require this overexpression of EphA2.

Recent reports from our laboratory and others have shown that many malignant epithelial cells express high levels of EphA2 that is not tyrosine phosphorylated. Previously, we had related these depressed levels of EphA2 tyrosine phosphorylation with decreased ligand binding. Malignant cells often have unstable cell-cell contacts and we postulated that this decreases the ability of EphA2 to stably interact with its ligands, which are anchored to the membrane of adjacent cell. In part, our present data suggests a new paradigm in which the phosphotyrosine content of EphA2 is also negatively regulated by an associated tyrosine phosphatase that is overexpressed in malignant cells. Given the relationship between EphA2 phosphorylation and cell-cell adhesion, we cannot exclude that cell-cell contacts could also regulate the expression or function of LMW-PTP and future investigation should address this possibility.

The fact that high levels of LMW-PTP were observed in several different cell models of metastatic cancer is notable given that LMW-PTP overexpression is sufficient to confer malignant transformation. LMW-PTP overexpressing cells gain the ability to colonize soft agar and acquire a malignant phenotype when cultured in three-dimensional basement membranes, such as Matrigel. Notably, however, LMW-PTP-overexpressing MCF-10A epithelial cells displayed reduced rates of cell growth as measured using two-dimensional assays of cell growth. This latter observation is consistent with recent reports that high levels of LMW-PTP similarly decrease the monolayer growth rates of other cell types (Shimizu, H., Shiota, M., Yamada, N., Miyazaki, K., Ishida, N., Kim, S. & Miyazaki, H. (2001) *Biochemical & Biophysical Research Communications* 289, 602-607; Fiaschi, T., Chiarugi, P., Buricchi, F., Giannoni, E., Taddei, M. L., Talini, D., Cozzi, G., Zecchi-Orlandini, S., Raugei, G. & Ramponi, G. (2001) *Journal of Biological Chemistry* 276, 49156-49163). Although such a finding had been interpreted to suggest that LMW-PTP might negatively regulate malignant transformation, our findings support a very different conclusion. Consistent with this, recent studies by our laboratory and others have shown that malignant transformation of MCF-10A cells is often accompanied by decreased monolayer growth rates and that the most aggressive variants of MCF-10A in vivo demonstrate the slowest growth in monolayer culture. These findings have important implications for the design and interpretation of oncogene function when using non-transformed epithelial cell systems.

The biochemical consequences of EphA2 tyrosine phosphorylation remain largely unclear. Unlike other receptor tyrosine kinases, where autophosphorylation is necessary for enzymatic activity, tyrosine phosphorylation of EphA2 is not required for its enzymatic activity. Consistent with our present results, EphA2 retains comparable levels of enzymatic activity in non-transformed and tumor-derived cells, despite dramatic differences in its phosphotyrosine content (Zantek, N. D., Azimi, M., Fedor-Chaiken, M., Wang, B., Brackenbury, R. & Kinch, M. S. (1999) *Cell Growth & Differentiation* 10, 629-638). Similarly, antibody-mediated stimulation of EphA2 autophosphorylation does not change the levels of EphA2 enzymatic activity. Phosphopeptide analyses of the EphA2 cytoplasmic domain provide one potential explanation. Although EphA2 has a predicted activation loop tyrosine at residue 772 (Lindberg, R. A. & Hunter, T. (1990) *Molecular & Cellular Biology* 10, 6316-6324), neither in vitro nor in vivo phosphopeptide analyses found that this site is not phosphorylated either in normal cell models or in response to exogenous ligands in malignant cell models. Thus, the lack of a consensus activation loop tyrosine may account for the retention of EphA2 enzymatic activity in cells where it is not tyrosine phosphorylated.

Whereas tyrosine phosphorylation of EphA2 does not appear to be necessary for its intrinsic enzymatic activity, ligand-mediated tyrosine phosphorylation regulates EphA2 protein stability. Specifically, tyrosine phosphorylation fates EphA2 to interact with the c-Cbl adapter protein and to subsequently be internalized and degraded within proteosomes (J. Walker-Daniels et al., Mol. Cancer Res. 2002 November; 1(1):79-87). Consequently, the phosphatase activity of LMW-PTP would be predicted to increase EphA2 protein stability. Indeed, the highest levels of EphA2 are consistently found in cells with high levels of LMW-PTP. One interesting implication of this finding is that it provides a mechanism, independent of genetic regulation of the EphA2 gene, to explain why high levels of EphA2 are found in many different tumors. An alternative possibility is that LMW-PTP upregulates EphA2 gene expression and our present findings do not formally eliminate this possibility. The fact that EphA2 inhibitors reversed the malignant character of LMW-PTP overexpressing cells suggests that the upregulation of EphA2 is relevant to the cellular behaviors of LMW-PTP-mediated transformation.

In summary, our present studies, as described in this example and in Kikawa et al., J. Biol. Chem. 277 (42): 39274-39279 (2002)) identify LMW-PTP as a new oncogene that is overexpressed in tumor-derived carcinoma cells. We also link the biochemical and biological actions of overexpressed LMW-PTP as with EphA2. These findings have important implications for understanding the biochemical and biological mechanisms that contribute to the metastatic progression of epithelial cells. Moreover, our present studies identify an important signaling system that could ultimately provide an opportunity to target the large number of cancer cells that overexpress EphA2 or LMW-PTP.

Example III

Effects of LMW-PTP Overexpression

Cell lines and reagents were as described in Example II (Kikawa et al., J. Biol. Chem. 277 (42): 39274-39279 (2002)). Methods for making cell lysates and for performing immunoprecipitation and western blot (immunoblot) analyses, EGTA and pervanadate treatments, transfection and selection, and growth assays were also as described in Example II ((Kikawa et al., J. Biol. Chem. 277 (42): 39274-39279 (2002)).

Morphological Effects of LMW-PTP Overexpression in Non-Transformed Cells

Monolayer cultures of MCF-10A cells that had been stably transfected with either wild-type human LMW-PTP, or a matching vector control, were subjected to microphotography (600×) (FIG. 10). Whereas the non-transformed (vector) cells retained a characteristic epithelial morphology, LMW-PTP-transfected cells adopted a mesenchymal phenotype that is characteristic of malignant epithelial cells. Overexpression of LMW-PTP was thus observed to alter two-dimensional morphology of the cells.

Figure 11:
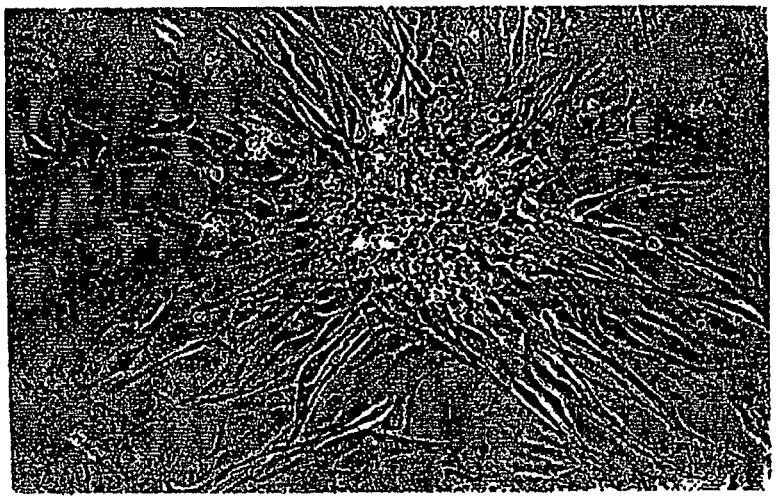
FIG. 11 shows that LMW-PTP overexpressing transfected MCF-10A cells form foci at high cell density.

The LMW-PTP transfected MCF-10A cells were further observed to form three-dimensional foci, a hallmark of malignant transformation, when cultured at high cell density (FIG. 11).

Effects of LMW-PTP Inactivation in Transformed Cells

To evaluate the biological outcomes of inhibiting LMW-PTP in tumor cells, highly invasive MDA-MB-231 cells were stably transfected with a mutant of LMW-PTP (D129A). D129A functions as a substrate trapping mutant and thereby competes away the activity of endogenous LMW-PTP in the tumor cells. It effectively inactivates LMW-PTP in the transformed cells.

Figure 12:
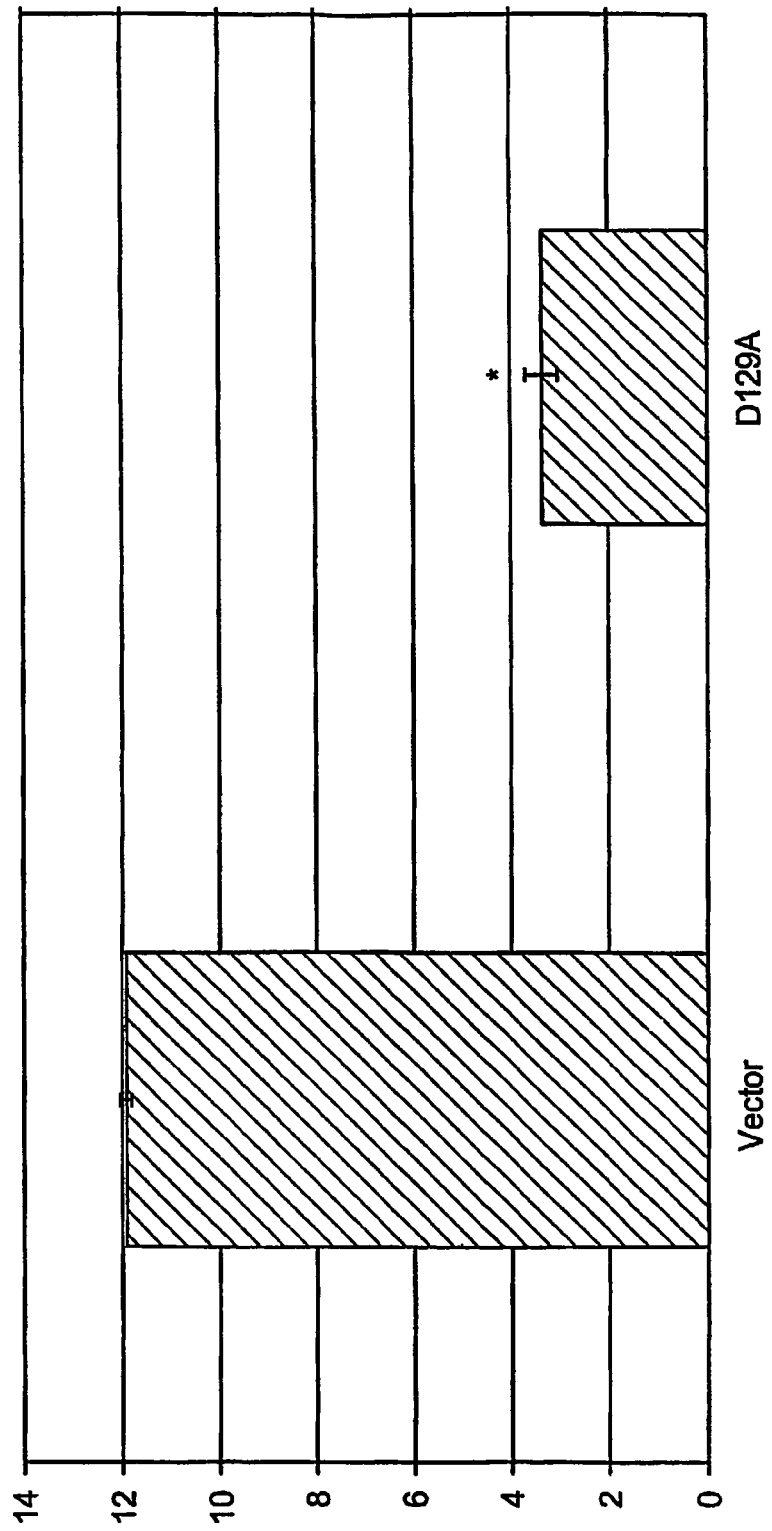
FIG. 12 shows that LMW-PTP inactivation in transformed cells results in decreased soft agar colonization.

D129A transfected cells showed reduced colony formation in soft agar relative to matched (vector) controls (FIG. 12). Thus LMW-PTP inactivation in transformed cells results in decreased soft agar colonization. This indicates that LMW-PTP is necessary for anchorage-independent cell growth and/or survival, which are hallmarks of malignant cells.

Figure 13:
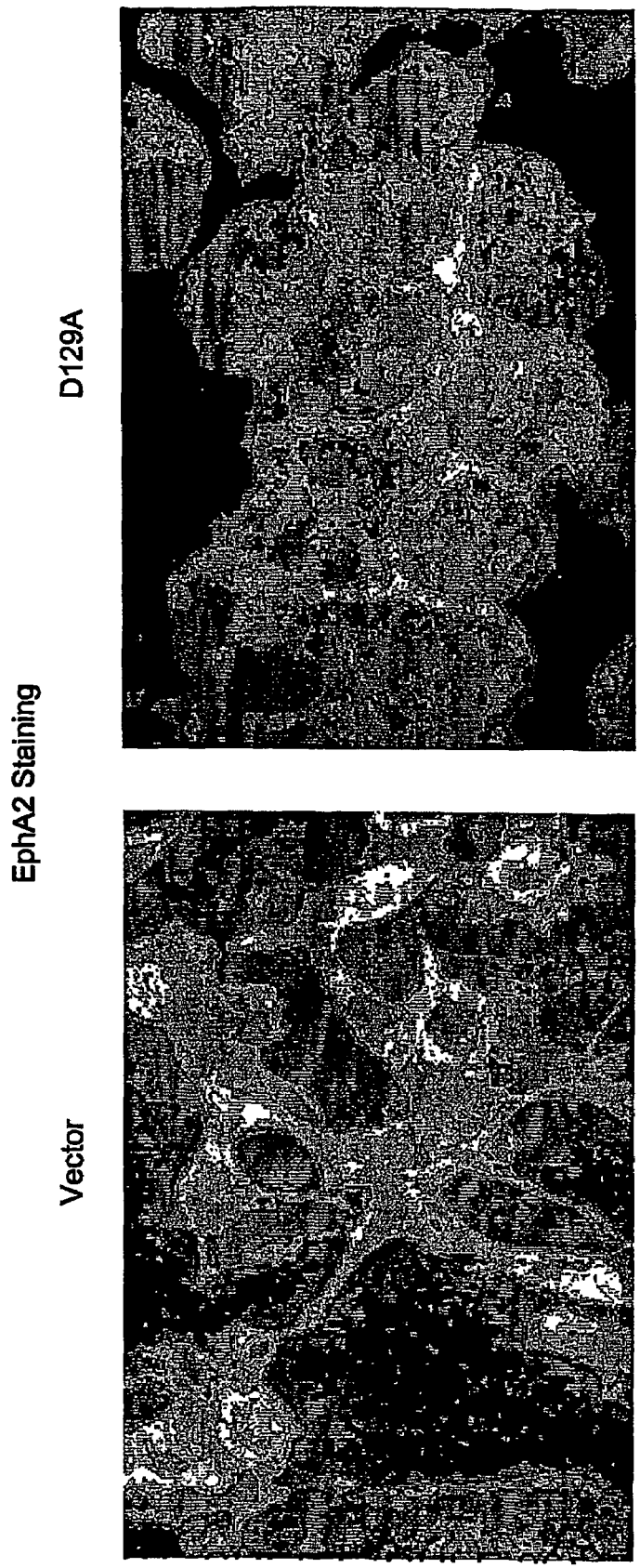
FIG. 13 shows that LMW-PTP inactivation in transformed cells alters two-dimensional morphology and EphA2 distribution.

It was also found that inactivation of LMW-PTP alters two-dimensional morphology and EphA2 distribution in transformed cells. The morphology of MDA-MB-231 cells that express dominant-negative LMW-PTP (D129A) or a matched vector control was evaluated by immunofluorescence microphotography of labeled EphA2 (FIG. 13). Control cultures MDA-MB-231 normally adopt a mesenchymal morphology with EphA2 diffusely distributed or enriched with membrane ruffles. In contrast, D129A-transfected cells display a characteristic epithelial morphology, with EphA2 enriched within sites of cell-cell contact.

Figure 14:
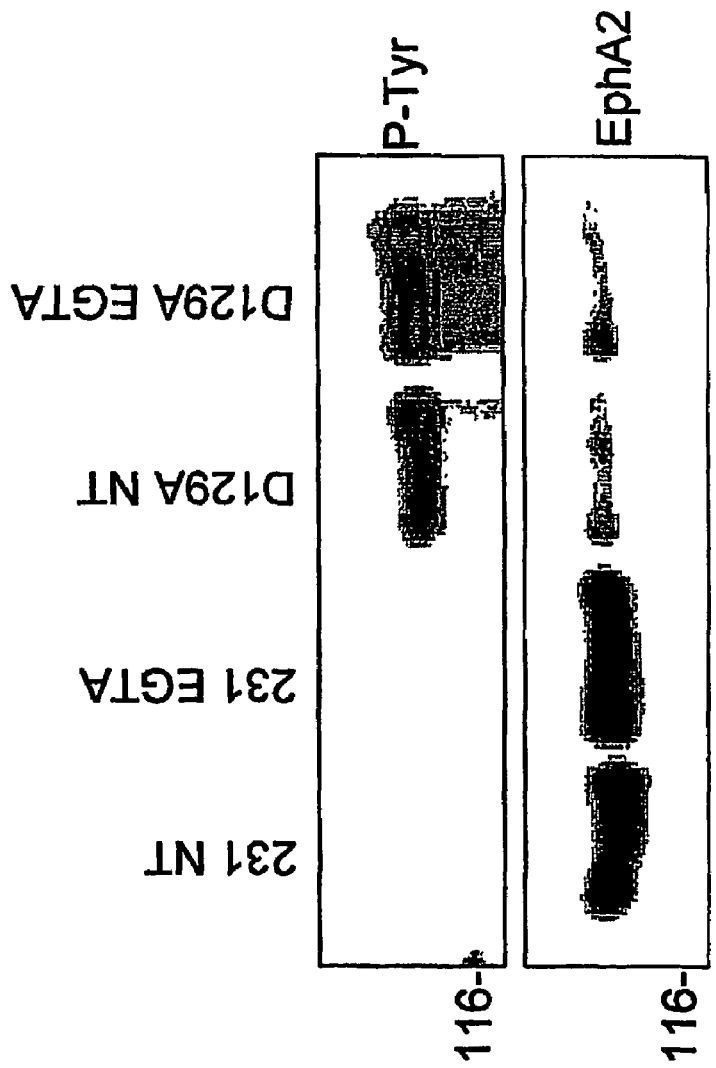
FIG. 14 shows the results of EGTA treatment of transformed cells that have been transfected with D129A to inactivate LMW-PTP.

D129A LMW-PTP MDA-MB-231 cells were treated with EGTA to determine its effect on the phosphorylation status of EphA2. Detergent extracts from $5 \times 10^6$ control and D129A-transfected MDA-MB-231 cells were harvested as described in Examples I and II. After immunoprecipitating EphA2 with D7 antibodies, the samples were resolved by SDS-PAGE and subjected to Western blot analyses with phosphotyrosine-specific (4G10) antibodies. The EphA2 in D129A-transfected cells was found to be more highly tyrosine phosphorylated, even following treatment with EGTA (FIG. 14). EGTA destabilizes cell-cell contacts and thereby prevent EphA2 from binding its membrane-anchored ligands. This suggests that D129A prevents EphA2 from being dephosphorylated even after loss of ligand binding.

FIG. 15 is a table that summarizes evidence from immunofluorescence microscopic studies using LMW-PTP transfected MCF-10A cells and D129A-transfected MDA-MB-231 (transformed) cells. The altered morphology and markers of LMW-PTP-transfected MCF-10A cells is consistent with malignant transformation. Moreover, the morphology of D129A overexpressing cells is consistent with a less aggressive (more differentiated) phenotype.

Co-Localization of EphA2 and LMW-PTP in Transformed and Nontransformed Cells

Figure 16A:
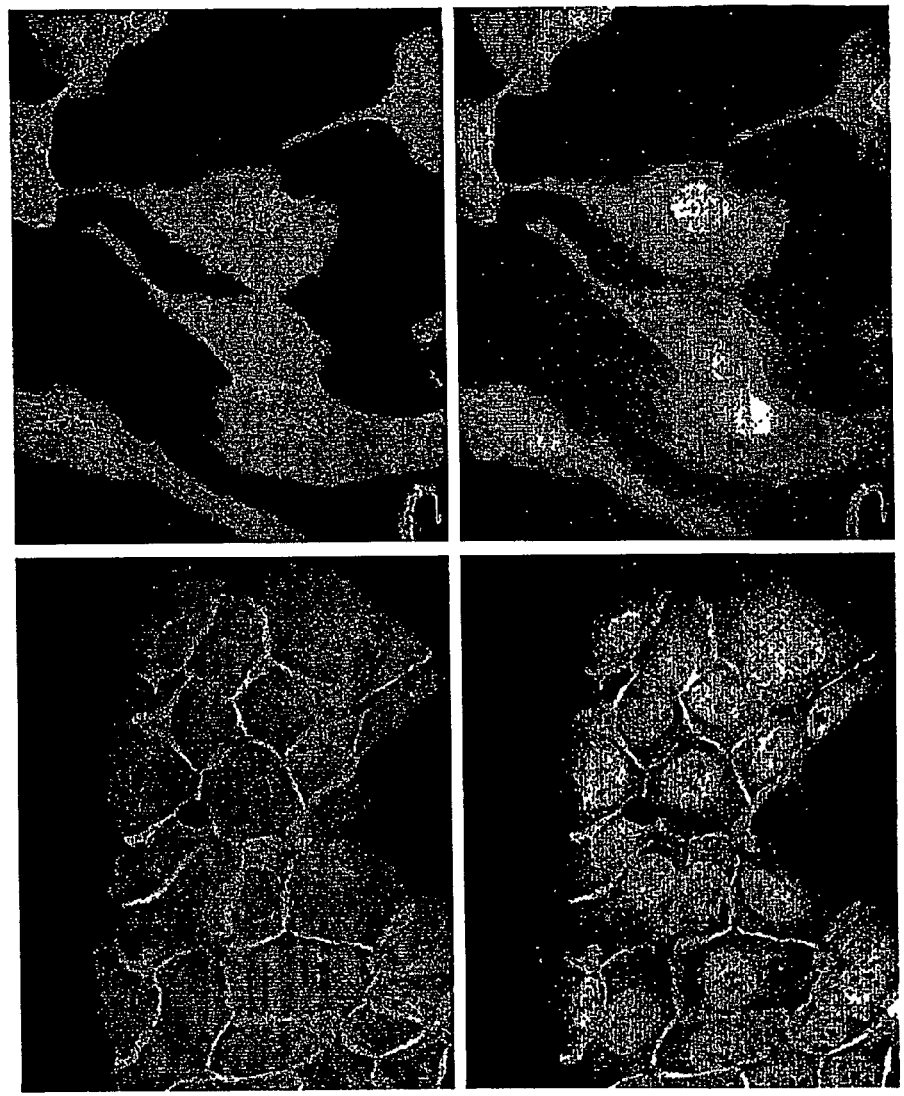
FIG. 16A shows co-localization of EphA2 and LMW-PTP in control and transfected MCF-10A cells.

Subcellular localization of EphA2 (using D7 antibodies) and LMW-PTP (using rabbit polyclonal sera) in control and LMW-transfected MCF-10A cells was evaluated in formalin-fixed (3.7%, 2 minutes), detergent permeabilized (PBS containing 0.5% Triton-X-100) monolayers, cultured on glass coverslips. The images (FIG. 16A) were viewed on a Nikon microscope (600×) and images captured using Nikon digital cameras and software.

Figure 16B:
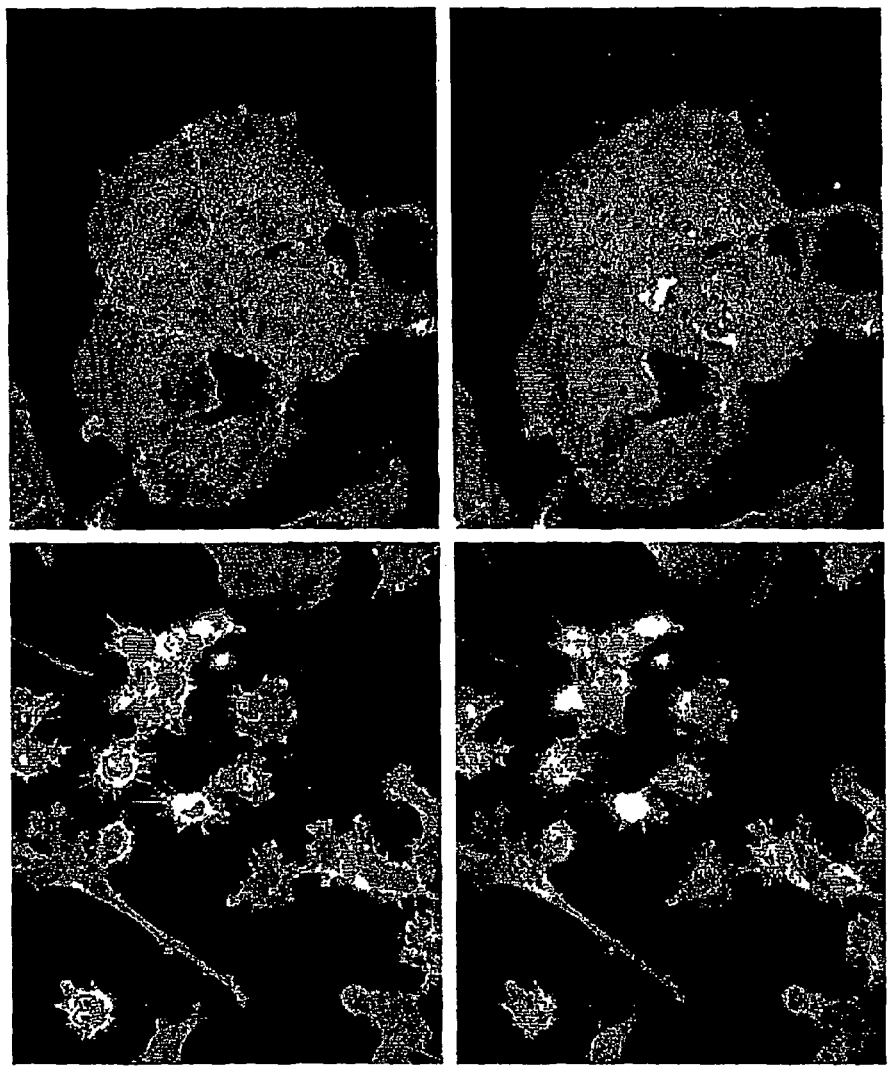
FIG. 16B shows co-localization of EphA2 and LMW-PTP in transformed cells that have been transfected with D129A to inactivate LMW-PTP.

Subcellular localization of EphA2 (using D7 antibodies) and LMW-PTP (using rabbit polyclonal sera) was likewise evaluated in control and D129A overexpressing MDA-MB-231 cells (FIG. 16B).

Figure 17:
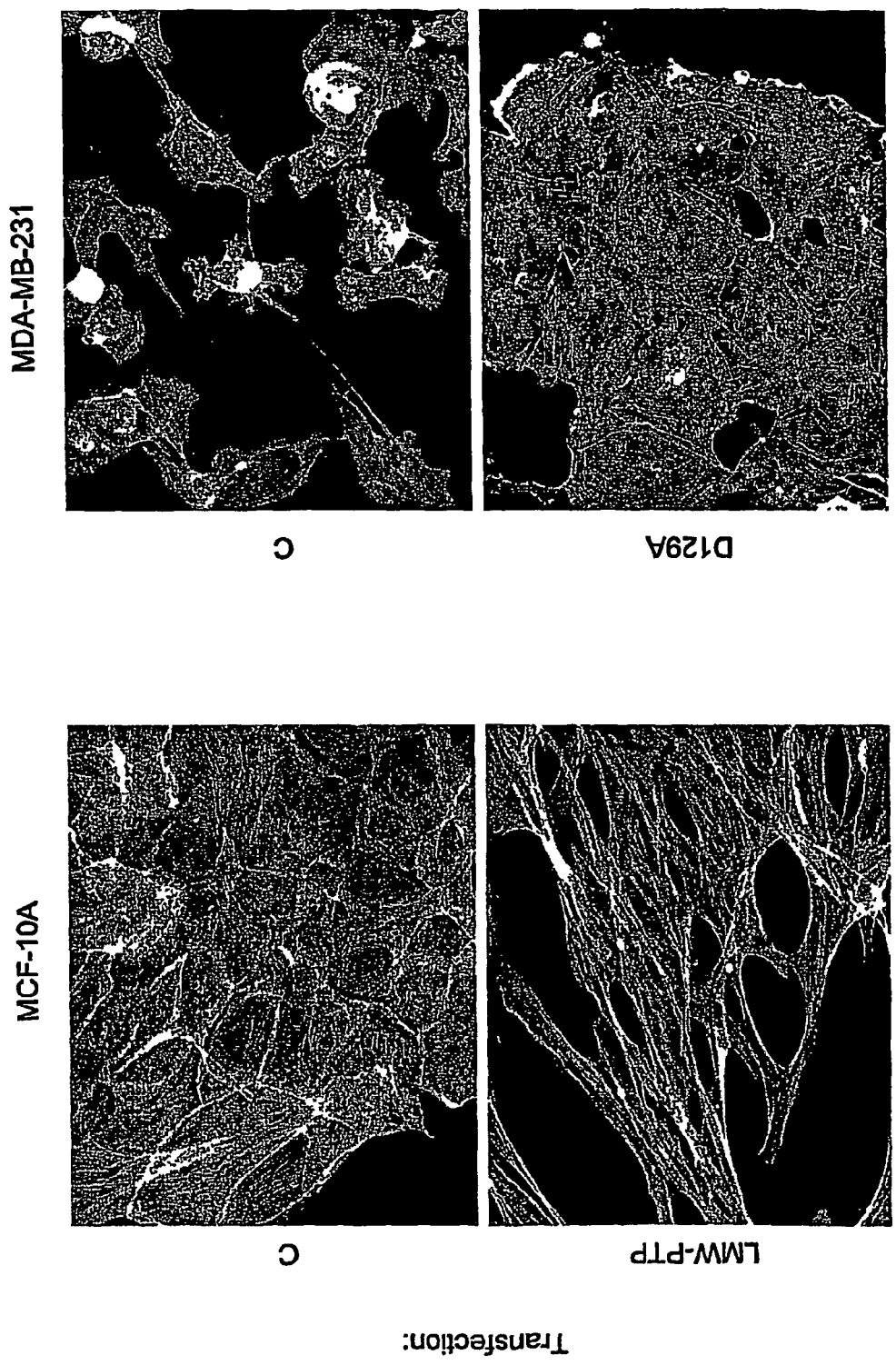
FIG. 17 shows that altered organization of actin cytoskeleton relates to LMW-PTP expression and function.

Effects of LMW-PTP Overexpression on Actin Organization in Transformed and Nontransformed Cells The organization of the actin cytoskeleton was evaluated in a MDA-MB-231 cell line stably expressing the D129A LMW-PTP mutation (B isoform), the MCF-10A cell line, and the MCF-10A cell line stably expressing the wild-type (WT) LMW-PTP molecule (B isoform) by immunofluorescence localization of fluorescein-conjugated phalloidin (Molecular Probes, Eugene, Oreg.). The subcellular localization of actin (phalloidin staining) was evaluated in formalin-fixed (3.7%, 2 minutes), detergent permeabilized (PBS containing 0.5% Triton-X-100) monolayers, cultured on glass coverslips. The images (FIG. 17) were viewed on a Nikon microscope (600×) and images captured using Nikon digital cameras and software.

Overexpression of wild-type LMW-PTP was found to cause the formation of stress fibers (as opposed to the adhesion belts that predominate in control cells). In the converse situation, dominant-negative inhibitors (D129A) of LMW-PTP decrease the number of stress fibers in MDA-MB-231. These observations are consistent with the hypothesis that wild-type LMW-PTP promotes a malignant (migratory and invasive) phenotype whereas inhibition of LMW-PTP is sufficient to reverse an aggressive phenotype.

Effects of LMW-PTP Overexpression on Focal Adhesion

Figure 18:
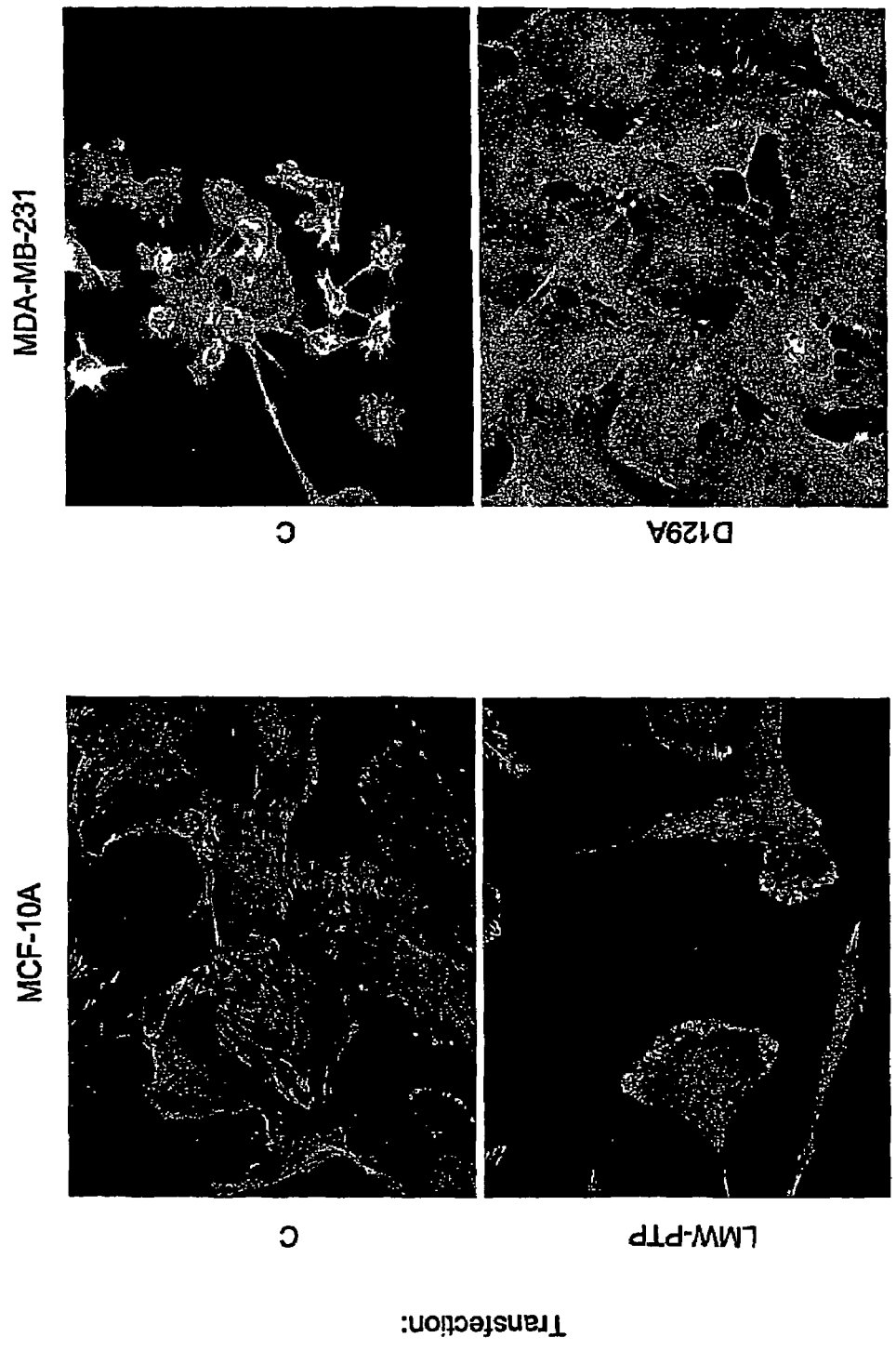
FIG. 18 shows that altered focal adhesion formation relates to LMW-PTP expression and function.

The organization of focal adhesion, as determined using paxillin-specific antibodies, was also evaluated in MDA-MB-231 cells by immunofluorescence microscopy. The subcellular localization of paxillin was evaluated in formalin-fixed (3.7%, 2 minutes), detergent permeabilized (PBS containing 0.5% Triton-X-100) monolayers, cultured on glass coverslips. The images (FIG. 18) were viewed on a Nikon microscope (600×) and images captured using Nikon digital cameras and software.

Overexpression of wild-type LMW-PTP was found to increase the prominence of focal adhesion, particularly at the leading edge of cell migration and invasion, which is consistent with a more aggressive phenotype. In the converse situation, dominant-negative inhibitors (D129A) of LMW-PTP decrease the predominance of focal adhesion in MDA-MB- 231 cells, resulting in a diffuse (rather than polarized) distribution of focal adhesions, which is not consistent with cell migration or invasion.

Pathological Markers of Malignant Character

Figure 19:
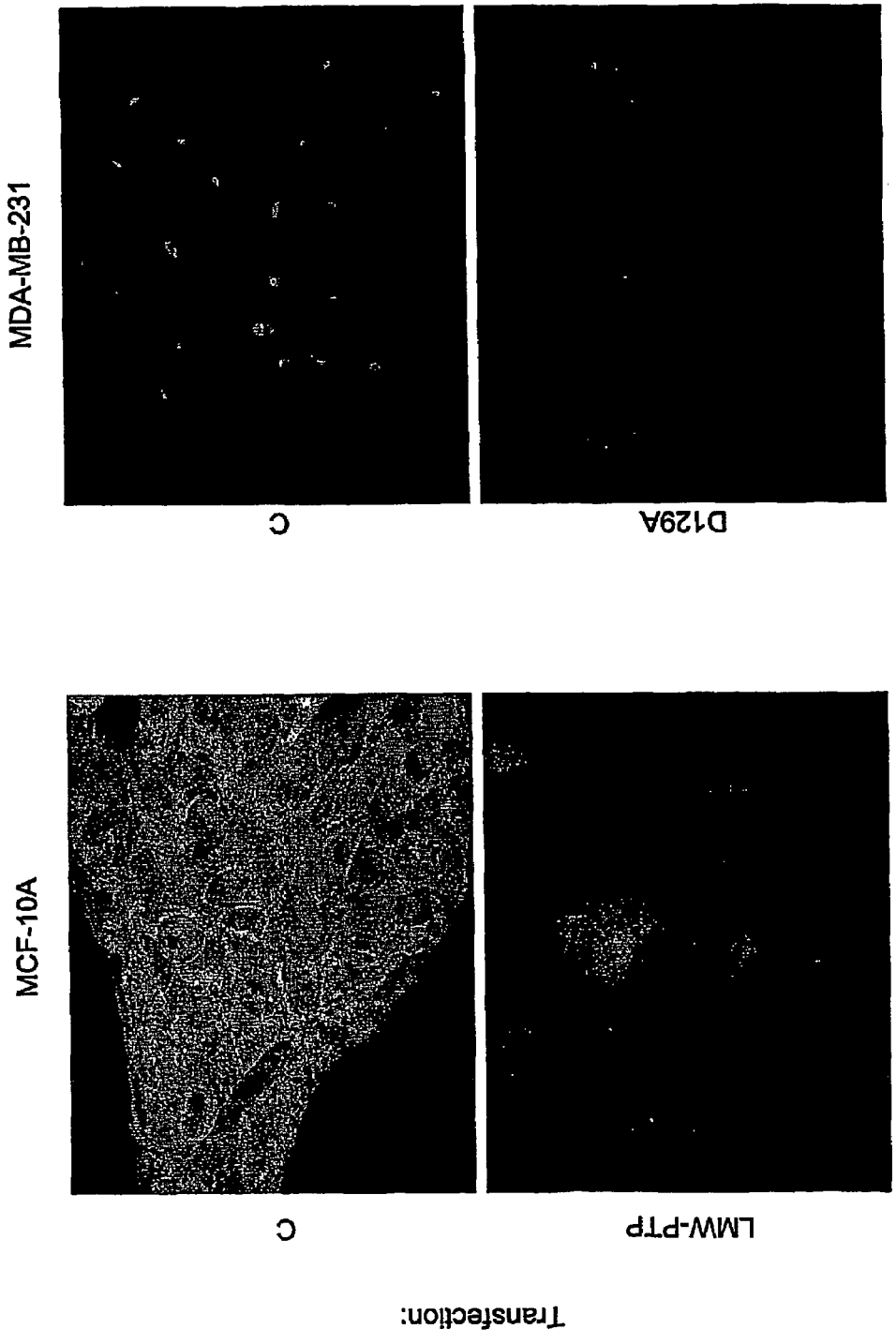
FIG. 19 shows cytokeratin expression altered by LMW-PTP expression.
Figure 20:
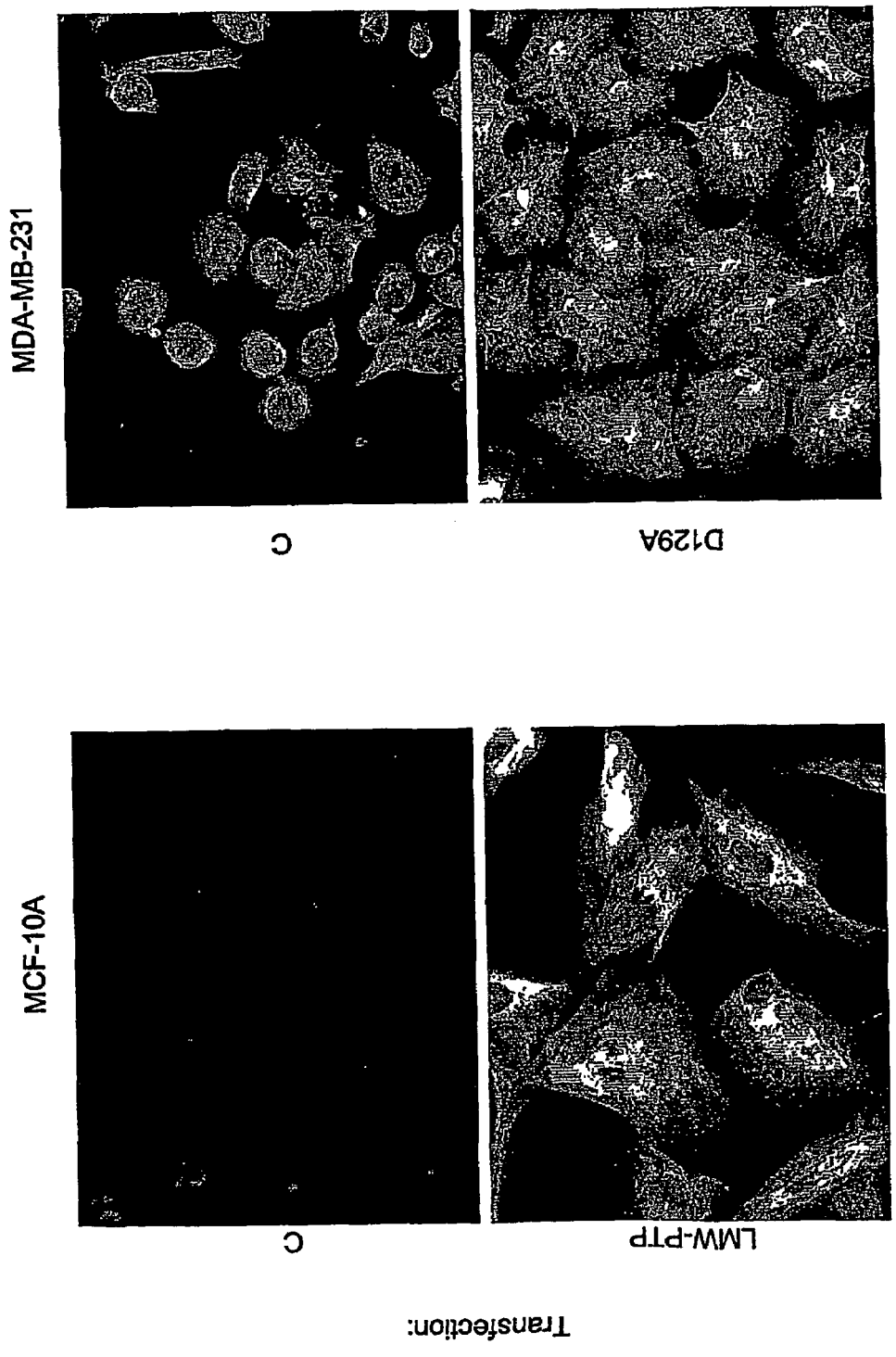
FIG. 20 shows vimentin expression altered by LMW-PTP expression.

The expression of cytokeratin (FIG. 19) and vimentin (FIG. 20) was evaluated using immunofluorescence microscopy. The staining of cytokeratin and vimentin was evaluated in formalin-fixed (3.7%, 2 minutes), detergent permeabilized (PBS containing 0.5% Triton-X-100) monolayers, cultured on glass coverslips. The images were viewed on a Nikon microscope (600×) and images captured using Nikon digital cameras and software.

Overexpression of wild-type LMW-PTP was found to decrease cytokeratin but increase vimentin expression. These results are notable given that these changes in intermediate filament protein expression are frequently used by pathologists for cancer diagnosis and typing.

Example IV

Effect of LMW-PTP Overexpression on Tumorigenic Potential of Non-Transformed Epithelial Cells Cells (MCF-10A, MCF-10A Neo (control) and transfected MCF-10A cells stably overexpressing wild-type LMW-PTP) were introduced into mice via subcutaneous injection. Two dosage levels were used: approximately 2 million and 5 million cells. Three mice were included in each group. The mice were observed 20 days after injection, and the size of the tumor (if present) was measured.

Figure 21:
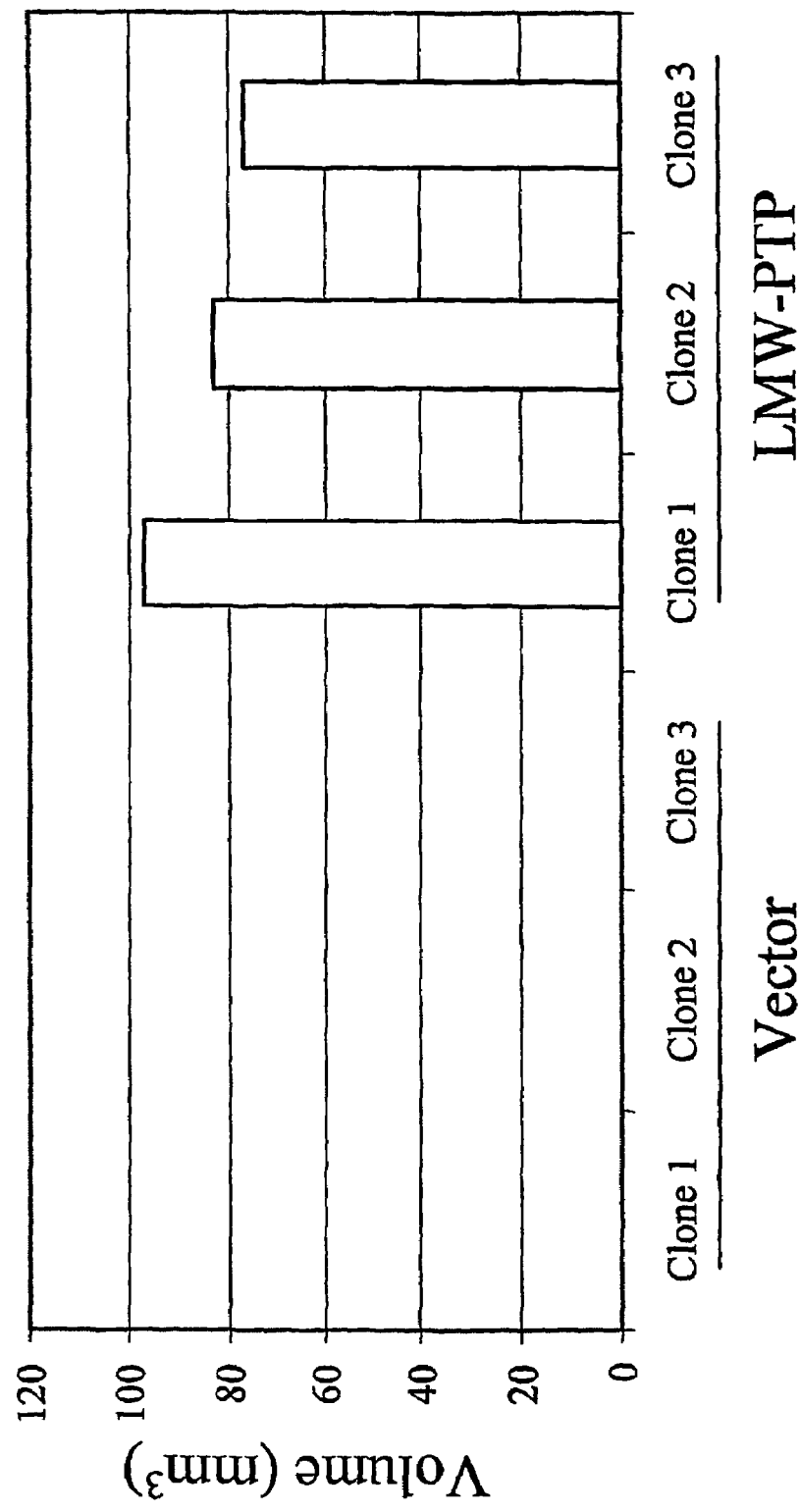
FIG. 21 shows data relating to tumor development in mice injected with $5 \times 10^6$ EphA2 overexpressing MCF-10A cells and controls, 20 days after injection.

FIG. 21 shows tumor measurement data for mice injected with $5 \times 10^6$ cells, observed 20 days post-injection. None of the mice injected with the parental MCF-10A cells or the control vector exhibited tumorogenesis at the injection site. Mice injected with the MCF-10A cells stably overexpressing WT LMW-PTP, however, exhibited significant growth in all 3 of the mice injected with 5 million cells, and 2 of the 3 mice injected with 1 million cells. These results suggest that LMW-PTP overexpression is sufficient to confer tumorigenic potential upon non-transformed epithelial cells. EphA2 is the only other oncogene we are aware of that is capable of conferring tumorigenic potential upon non-transformed epithelial cells.

The complete disclosure of all patents, patent applications, and publications, and electronically available material (including, for example, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for treating cancer in a mammal comprising a cancer cell that expresses a low molecular weight protein tyrosine kinase (LMW-PTP), the method comprising administering to the mammal a treatment agent comprising a mutant LMW-PTP protein D129A in an amount effective to inhibit the activity of LMW-PTP.

2. A method for treating cancer in a mammal comprising a cancer cell that expresses a low molecular weight protein tyrosine kinase (LMW-PTP) and an EphA2 receptor molecule, the method comprising administering to the mammal a first treatment agent comprising a mutant LMW-PTP protein D129A in an amount effective to inhibit the activity of LMW-PTP and a second treatment agent comprising an anti-EpbA2 antibody or an ephrinA1 linand in an amount effective to favorably alter the biological activity of the EphA2 receptor molecule.

3. The method of claim 2 wherein the first and second treatment agents are delivered simultaneously.

4. The method of claim 2 wherein the first treatment agent is delivered prior to the second treatment agent.

5. The method of claim 2 wherein the second treatment agent is delivered prior to the first treatment agent.

6. The method of claim 2 wherein favorably altering the biological activity of the EpbA2 receptor molecule comprises increasing the phosphotyrosine content of the EphA2 receptor molecule.

7. The method of claim 1 or 2 wherein at least one treatment agent is covalently linked to a cytotoxic agent.

8. The method of claim 1 or 2 wherein the cancer cell is a metastatic carcinoma cell.

9. A method for diagnosing cancer in a mammal comprising:
lysing cells in a biological material obtained from the mammal to yield a cell lysate;
contacting the cell lysate with an antibody that binds LMW-PTP to form a bound complex;
detecting the bound complex; and
determining whether LMW-PTP is overexpressed in the biological material relative to a noncancerous biological material, wherein overexpression of LMW-PTP is indicative of the presence of cancer cells in the mammal.

10. A method for diagnosing cancer in a mammal comprising: assaying a biological material comprising cells of the mammal for LMW-PTP activity; and
determining whether LMW-PTP is overexpressed in the biological material relative to a noncancerous biological material, wherein overexpression of LMW-PTP is indicative of the presence of cancer cells in the mammal.

11. The method of claim 10 wherein the biological material is in the mammal.

12. The method of claims 9 or 10 wherein the biological material comprises a tissue, organ, blood, urine, saliva, or spinal fluid of the mammal.

13. The method of claim 12 wherein the biological material is obtained from the mammal.

14. The method of claim 13 further comprising obtaining the biological material from the mammal.

15. A method for evaluating the efficacy of a candidate cancer therapeutic agent that targets the EphA2 receptor molecule, the method comprising:
contacting a cancer cell expressing EphA2 receptor molecule and LMW-PTP with a candidate therapeutic agent to yield a treated cancer cell;
determining the amount or activity of LMW-PTP in the treated cancer cell; and
comparing the amount or activity of LMW-PTP in the treated cancer cell with the amount or activity of LMW-PTP in an analogous untreated cancer cell, wherein a reduction in the amount or activity of LMW-PTP in the treated cell is indicative of the efficacy of EphA2 targeting of the candidate therapeutic agent.

* * * * *